United States Patent [19]
Kouji et al.

[11] Patent Number: 4,964,905
[45] Date of Patent: Oct. 23, 1990

[54] N-SUBSTITUTED-PHENYLTERACONIMIDE COMPOUND, HERBICIDAL COMPOSITION, AND METHOD FOR THE DESTRUCTION OF UNDESIRABLE WEEDS

[75] Inventors: Hiroyuki Kouji; Teruyuki Misumi, both of Yokohama, Japan

[73] Assignee: Asahi Kasei Kogyo Kabushiki Kaisha, Osaka, Japan

[21] Appl. No.: 826,608

[22] Filed: Feb. 6, 1986

[30] Foreign Application Priority Data

Feb. 7, 1985 [JP] Japan ................................. 60-20984
Mar. 15, 1985 [JP] Japan ................................. 60-50584
Mar. 19, 1985 [JP] Japan ................................. 60-53280
Nov. 29, 1985 [JP] Japan ................................ 60-267244

[51] Int. Cl.$^5$ ............... C07D 207/325; C07D 413/10; A01N 37/24
[52] U.S. Cl. ................................ 71/95; 71/88; 548/545; 548/546; 544/143
[58] Field of Search ............... 548/545, 546, 5; 71/95, 71/88; 544/143

[56] References Cited
U.S. PATENT DOCUMENTS 3,138,523  6/1964  Schmeling ......................... 548/545
3,636,044  1/1972  Fujinnami et al. ................. 548/545
3,878,224  4/1975  Matsui et al. ...................... 71/94 X

FOREIGN PATENT DOCUMENTS 0068822  1/1983  European Pat. Off. .
1919851  10/1970  Fed. Rep. of Germany .
1310442  10/1962  France ............................. 71/95
0019503  11/1966  Japan ............................... 548/547
58-114298  1/1985  Japan .
1103801  5/1986  Japan ............................... 71/95
0190755  8/1986  Japan ............................... 71/95

Primary Examiner—David B. Springer
Attorney, Agent, or Firm—Birch, Stewart, Kolasch & Birch

[57] ABSTRACT

An N-substituted-phenylteraconimide compound represented by the formula

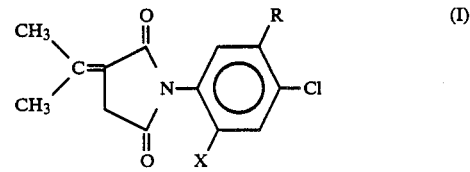

wherein X and R are as defined in the disclosure, herbicidal composition and method for the destruction of undesirable weeds. The herbicides comprising the above compounds are capable of selectively controlling undesirable weeds among desirable crop plants.

25 Claims, No Drawings

N-SUBSTITUTED-PHENYLTERACONIMIDE COMPOUND, HERBICIDAL COMPOSITION, AND METHOD FOR THE DESTRUCTION OF UNDESIRABLE WEEDS

FIELD OF THE INVENTION

This invention relates to a novel compound which exhibits a high herbicidal activity with high selectivity, a novel herbicidal composition comprising as an active ingredient the novel compound which is useful as an effective herbicide for various crops and a method for the destruction of undesirable weeds using the novel herbicidal composition. More particularly, the present invention is concerned with an N-substituted-phenylteraconimide compound, a herbicidal composition comprising the compound and a method for the destruction of undesirable weeds using the herbicidal composition.

DESCRIPTION OF THE PRIOR ART

Up to now, a herbicide comprising as an active ingredient an N-substituted-phenyl-3,4,5,6-tetrahydrophthalimide compound is generally well known as an imide type herbicide to exhibit a high herbicidal activity (see, for example, U.S. Pat. No. 3,878,224).

However, the known imide type herbicides generally tend to be excellent in herbicidal activity but poor in selectivity. Hence, they are not suitable for practical use.

The ideal herbicide should be one which further satisfies the following conditions in addition to the above-stated excellent herbicidal activity and high selectivity. The toxicity of the herbicide to warm-blooded animals must be low. The herbicide is effective even if it is applied any time through the whole period of growth of crop plants. Moreover, after usage, the herbicide decomposes as promptly as possible so that it does not contaminate the soil. However, such an ideal imide type herbicide which satisfies the above conditions is not yet known.

OBJECT OF THE INVENTION

Under the above-stated current situation, the inventors have conducted intensive studies to develop a novel imide type herbicide which is free from the drawbacks accompanying the conventional imide type herbicides, which has selective and high herbicidal activity that means complete safety to crop plants and prompt elimination of any unnecessary weeds present therewith, which can be used continuously through the whole period of growth of crop plants. As a result, it has been found that a novel N-substituted-phenylteraconimide compound satisfies the above-mentioned requirements for an improved herbicide, and that the compound, even at a low dosage, is very effective for a wide spectrum of crop plants, such as rice, wheat, corn, soybean and cotton plants. Based on this novel finding, the present invention has been completed.

Accordingly, it is an object of the present invention to provide a novel N-substituted-phenylteraconimide compound having a high selectivity as well as a high herbicidal activity.

It is another object of the present invention to provide a novel herbicidal composition containing the novel compound.

It is a further object of the present invention to provide a method for the destruction of undesirable weeds using the novel herbicidal composition.

DESCRIPTION OF THE INVENTION

In one aspect of this invention, there is provided an N-substituted-phenylteraconimide compound represented by the formula

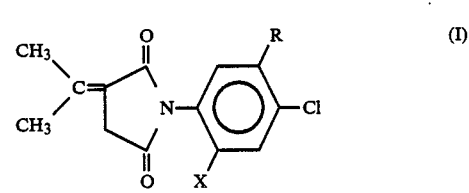

wherein X represents a hydrogen atom, a fluorine atom or a chlorine atom; and

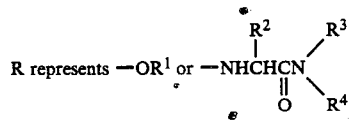

in which $R^1$ represents a hydrogen atom, a straight chain or branched alkyl group having up to 8 carbon atoms, a straight chain or branched alkenyl group having up to 8 carbon atoms, an alkynyl group having up to 8 carbon atoms, a cycloalkyl group having up to 8 carbon atoms wherein a carbon atom thereof is unsubstituted or substituted with an oxygen atom, a sulfur atom or a carbonyl group, or a straight chain or branched alkyl or alkenyl group having up to 8 carbon atoms and substituted with at least one substituent selected from the group consisting of a halogen atom, a cyano group, a hydroxyl group, an alkoxyl group having up to 8 carbon atoms, an alkylthio group having up to 8 carbon atoms, an epoxy group, a substituted or unsubstituted aromatic hydrocarbon group having up to 8 carbon atoms, an acyl group having up to 8 carbon atoms and an alkoxycarbonyl group having up to 8 carbon atoms, $R^2$ represents a hydrogen atom or a straight chain or branched alkyl group having up to 8 carbon atoms, and $R^3$ and $R^4$ each independently represent a hydrogen atom, a straight chain or branched alkyl group having up to 8 carbon atoms, a straight chain or branched alkenyl group having up to 8 carbon atoms, an alkynyl group having up to 8 carbon atoms, an alkoxyl group having up to 8 carbon atoms, an alkoxyalkyl group having up to 8 carbon atoms, an alkoxycarbonylalkyl group having up to 8 carbon atoms, a cycloalkyl group having up to 8 carbon atoms, a hydroxyalkyl group having up to 8 carbon atoms, a cyanoalkyl group having up to 8 carbon atoms, an aralkyl group having up to 9 carbon atoms or an aryl group having up to 8 carbon atoms, or $R^3$ and $R^4$ are directly bonded with each other, thereby forming with the nitrogen atom bonded therewith a heterocyclic ring group having up to 7 carbon atoms, in the skeleton of which an oxygen atom is contained or not contained.

The characteristic feature of the compound of the present invention resides in that it has, in its molecular structure, an isopropylidene group as a substituent, as opposed to the conventional herbicides. It is quite unexpected that the introduction of the substituent enables the compound of the present invention to provide a herbicide which has a largely improved selectivity, such a high selectivity being never attained by the conventional imide type herbicides, and effectively eliminates undesirable weeds present with various crop plants by either preemergence or postemergence application.

In $R^1$ of the above formula (I), the straight chain or branched alkyl group having up to 8 carbon atoms may be, for example, methyl, ethyl, n-propyl, iso-propyl, n-butyl, sec-butyl, iso-butyl, n-amyl, iso-amyl, n-hexyl, n-heptyl, n-octyl and the like. The straight chain or branched alkenyl group having up to 8 carbon atoms may be, for example, allyl, crotyl, methallyl, 1-methyl-2-propenyl, 3-methyl-2-butenyl and the like. The alkynyl group having up to 8 carbon atoms may be, for example, propargyl, 1-methyl-2-propynyl, 1,1-dimethylpropynyl, 2-butynyl and the like. The cycloalkyl group having up to 8 carbon atoms may be, for example, cyclopropyl, cyclobutyl, cyclopentyl, cyclohexyl and the like. The cycloalkyl group having up to 8 carbon atoms wherein a carbon atom thereof is substituted with an oxygen atom, a sulfur atom or a carbonyl group may be, for example, 2-tetrahydropyranyl, 2-oxocyclopentyl, 2-oxocyclohexyl, 2-tetrahydrothiopyran and the like. The substituted straight chain or branched alkyl or alkenyl group may be, for example, 2-chloroethyl, 2-bromoethyl, 3-chloro-2-propenyl (cys isomer), 3-chloro-2-propenyl (trans isomer), 3-chloro-2-butenyl (cis isomer), 3-chloro-2-butenyl (trans isomer), 2-chloro-2-propenyl, 2,2,2-trifluoroethyl, 2-chloropropyl, cyanomethyl, 1-cyanoethyl, 2-cyanoethyl, 2hydroxyethyl, 2-hydroxypropyl, methoxyethyl, ethoxyethyl, methoxymethyl, ethoxymethyl, propoxymethyl, methylthiomethyl, ethylthiomethyl, methylthioethyl, ethylthioethyl, 2,3-epoxypropyl, 2,3-epoxybutyl, benzyl, 1-methylbenzyl, phenethyl, p-chlorobenzyl, p-methylbenzyl, p-methoxybenzyl, cinnamyl, phenacyl, acetonyl, 2-oxobutyl, methoxycarbonylmethyl, ethoxycarbonylmethyl, 1-methoxycarbonylethyl, 1-ethoxycarbonylethyl, 2-methoxycarbonylethyl, 1-methyl-1-methoxycarbonylethyl, 1-methyl-1-ethoxycarbonylethyl, 3-methoxycarbonyl-2-propenyl, 3-ethoxycarbonyl-2-propenyl, 2,2-dimethoxyethyl, 2,2-diethoxyethyl, 1,1-dimethoxyethyl, 1-methoxy-1-methoxycarbonylmethyl, 1-methoxy-1-ethoxycarbonylmethyl and the like.

In $R^2$ of the formula (I), the straight chain or branched alkyl group having up to 8 carbon atoms may be, for example, those as mentioned above with respect to $R^1$.

In $R^3$ and $R^4$ of the formula (I), the straight chain or branched alkyl group having up to 8 carbon atoms may be, for example, methyl, ethyl, n-propyl, iso-propyl, n-butyl, sec-butyl, iso-butyl, n-amyl, iso-amyl, n-hexyl and the like. The straight chain or branched alkenyl group having up to 8 carbon atoms may be, for example, allyl, crotyl, methallyl, 1-methyl-2-propenyl and the like. The alkynyl group having up to 8 carbon atoms may be, for example, those as mentioned above with respect to $R^1$. The alkoxyl group having up to 8 carbon atoms may be, for example, methoxy, ethoxy, n-propoxy, iso-propoxy, n-butoxy, iso-butoxy, sec-butoxy and the like. The alkoxyalkyl, alkoxycarbonylalkyl, carbonylalkyl, cycloalkyl, hydroxyalkyl and cyanoalkyl groups respectively having up to 8 carbon atoms may be, for example, those as mentioned above with respect to $R^1$, respectively. The aralkyl group having up to 9 carbon atoms may be, for example, benzyl, 1-methylbenzyl, phenethyl and the like. The aryl group having up to 8 carbon atoms may be, for example, phenyl, p-chlorophenyl, p-tolyl and the like.

In the above formula (I), when either of $R^3$ and $R^4$ represents a straight chain or branched alkyl group having up to 8 carbon atoms and the other represents a straight chain or branched alkyl group having up to 8 carbon atoms, an alkoxyl group having up to 8 carbon atoms or an alkoxyalkyl group having up to 8 carbon atoms, they have their respective free terminal ends or they are directly bonded with each other, thereby forming with the nitrogen atom bonded therewith a heterocyclic ring group having up to 7 carbon atoms. The heterocyclic ring group formed by $R^3$, $R^4$ and the nitrogen atom may be, for example, piperidino, morpholino, pipecolino, pyrrolidino, oxazolidino and the like.

In $R^1$ of the above formula (I), the alkyl group preferablly has up to 6 carbon atoms; the alkenyl, alkynyl, alkoxy and alkylthio groups preferably have up to 4 carbon atoms, respectively; the cycloalkyl group preferably has 3 to 6 carbon atoms; the acyl group preferably has 2 to 7 carbon atoms; the aromatic hydrocarbon group preferably has 6 to 8 carbon atoms; and the alkoxycarbonyl group preferably has 2 to 5 carbon atoms. In $R^2$ of the formula (I), the alkyl group preferably has up to 6 carbon atoms. In $R^3$ and $R^4$ of the formula (I), the alkyl group preferably has up to 6 carbon atoms; the alkenyl group preferably has 3 to 4 carbon atoms; the alkynyl and alkoxycarbonylalkyl groups preferably has 3 to 5 carbon atoms, respectively; the alkoxy group preferably has up to 4 carbon atoms; the alkoxyalkyl group preferably has 2 to 4 carbon atoms; the cycloalkyl group preferably has 3 to 6 carbon atoms; the hydroxyalkyl and cyanoalkyl groups preferably has 2 to 4 carbon atoms, respectively; the aralkyl group preferably has 7 to 9 carbon atoms; and the aryl group preferably has 6 to 8 carbon atoms.

As specific examples of the compound of the present invention represented by the general formula (I), there may be mentioned:

N-(2,4-dichloro-5-hydroxyphenyl)teraconimide,
N-(2,4-dichloro-5-methoxyphenyl)teraconimide,
N-(2,4-dichloro-5-ethoxyphenyl)teraconimide,
N-(2,4-dichloro-5-n-propoxyphenyl)teraconimide,
N-(2,4-dichloro-5-n-butoxyphenyl)teraconimide,
N-(2,4-dichloro-5-n-hexyloxyphenyl)teraconimide,
N-(2,4-dichloro-5-n-heptyloxyphenyl)teraconimide,
N-(2,4-dichloro-5-n-octyloxyphenyl)teraconimide,
N-(2,4-dichloro-5-isopropoxyphenyl)teraconimide,
N-(2,4-dichloro-5-isobutoxyphenyl)teraconimide,
N-(2,4-dichloro-5-sec-butoxyphenyl)teraconimide,
N-(2,4-dichloro-5-allyloxyphenyl)teraconimide,
N-(2,4-dichloro-5-crotyloxyphenyl)teraconimide,
N-(2,4-dichloro-5-methallyloxyphenyl)teraconimide,
N-[2,4-dichloro-5-(1-methylallyloxy)phenyl]teraconimide,
N-(2,4-dichloro-5-propargyloxyphenyl)teraconimide,
N-(2,4-dichloro-5-cyclopropyloxyphenyl)teraconimide,
N-(2,4-dichloro-5-cyclopentyloxyphenyl)teraconimide,
N-(2,4-dichloro-5-cyclohexyloxyphenyl)teraconimide,
N-[2,4-dichloro-5-(2-fluoroethyloxy)phenyl]teraconimide, N-[2,4-dichloro-5-(2-chloroethyloxy)phenyl]-teraconimide,
N-[2,4-dichloro-5-(2-bromoethyloxy)phenyl]-teraconimide,
N-[2,4-dichloro-5-(2,2,2-trifluoroethyloxy)phenyl]-teraconimide,
N-(2,4-dichloro-5-trifluoromethyloxyphenyl)-teraconimide,
N-(2,4-dichloro-5-difluoromethyloxyphenyl)-teraconimide,
N-[2,4-dichloro-5-(2-cyanoethyloxy)phenyl]-teraconimide,
N-[2,4-dichloro-5-(1-cyanoethyloxy)phenyl]-teraconimide,
N-(2,4-dichloro-5-cyanomethyloxyphenyl)teraconimide,
N-[2,4-dichloro-5-(2-hydroxyethyloxy)phenyl]-teraconimide,
N-[2,4-dichloro-5-(2-methoxyethyloxy)phenyl]-teraconimide,
N-[2,4-dichloro-5-(2-ethoxyethyloxy)phenyl]-teraconimide,
N-[2,4-dichloro-5-(2-isopropoxyethyloxy)phenyl]-teraconimide,
N-[2,4-dichloro-5-(2-methylthioethyloxy)phenyl]-teraconimide
N-[2,4-dichloro-5-(2-ethylthioethyloxy)phenyl]-teraconimide,
N-[2,4-dichloro-5-(2,3-epoxypropyloxy)phenyl]-teraconimide,
N-[2,4-dichloro-5-(α-methylbenzyloxy)phenyl]-teraconimide,
N-(2,4-dichloro-5-benzyloxyphenyl)teraconimide,
N-(2,4-dichloro-5-phenethyloxyphenyl)teraconimide,
N-[2,4-dichloro-5-(p-chlorobenzyloxy)phenyl]-teraconimide,
N-[2,4-dichloro-5-(1-methoxycarbonylethyloxy)-phenyl]-teraconimide,
N-[2,4-dichloro-5-(1-ethoxycarbonylethyloxy)-phenyl]-teraconimide,
N-(2,4-dichloro-5-methoxycarbonylmethyloxy-phenyl)teraconimide,
N-(2,4-dichloro-5-ethoxycarbonylmethyloxyphenyl)-teraconimide,
N-(2,4-dichloro-5-methylcarbonylmethyloxyphenyl)-teraconimide,
N-(2,4-dichloro-5-phenylcarbonylmethyloxyphenyl)-teraconimide,
N-(2,4-dichloro-5-n-amyloxyphenyl)teraconimide,
N-(2,4-dichloro-5-isoamyloxyphenyl)teraconimide,
N-[2,4-dichloro-5-(1-methoxy-1-methoxycarbonylmethyloxy)phenyl]-teraconimide,
N-(4-chloro-5-hydroxyphenyl)teraconimide,
N-(4-chloro-5-methoxyphenyl)teraconimide,
N-(4-chloro-5-ethoxyphenyl)teraconimide,
N-(4-chloro-5-n-propoxyphenyl)teraconimide,
N-(4-chloro-5-n-butoxyphenyl)teraconimide,
N-(4-chloro-5-isopropoxyphenyl)teraconimide,
N-(4-chloro-5-isobutoxyphenyl)teraconimide,
N-(4-chloro-5-sec-butoxyphenyl)teraconimide,
N-(4-chloro-5-allyloxyphenyl)teraconimide,
N-(4-chloro-5-crotyloxyphenyl)teraconimide,
N-(4-chloro-5-methallyloxyphenyl)teraconimide,
N-[4-chloro-5-(1-methylallyloxy)phenyl]-teraconimide,
N-(4-chloro-5-cyclohexyloxyphenyl)teraconimide,
N-[4-chloro-5-(2-fluoroethyloxy)phenyl]-teraconimide,
N-[4-chloro-5-(2-chloroethyloxy)phenyl]-teraconimide,
N-[4-chloro-5-(2-bromoethyloxy)phenyl]-teraconimide,
N-[4-chloro-5-(2,2,2-trifluoroethyloxy)phenyl]-teraconimide,
N-(4-chloro-5-trifluoromethyloxyphenyl)teraconimide,
N-(4-chloro-5-difluoromethyloxyphenyl)teraconimide,
N-[4-chloro-5-(2-cyanoethyloxy)phenyl]-teraconimide,
N-[4-chloro-5-(1-cyanoethyloxy)phenyl]-teraconimide,
N-[4-chloro-5-cyanomethyloxyphenyl)teraconimide,
N-[4-chloro-5-(2-hydroxyethyloxy)phenyl]-teraconimide,
N-[4-chloro-5-(2-methoxyethyloxy)phenyl]-teraconimide,
N-[4-chloro-5-(2-ethoxyethyloxy)phenyl]-teraconimide,
N-[4-chloro-5-(2-isopropoxyethyloxy)phenyl]-teraconimide,
N-[4-chloro-5-(2-methylthioethyloxy)phenyl]-teraconimide,
N-[4-chloro-5-(2-ethylthioethyloxy)phenyl]-teraconimide,
N-[4-chloro-5-(2,3-epoxypropyloxy)phenyl]-teraconimide,
N-[4-chloro-5-(α-methylbenzyloxy)phenyl]-teraconimide,
N-(4-chloro-5-benzyloxyphenyl)teraconimide,
N-(4-chloro-5-phenethyloxyphenyl)teraconimide,
N-[4-chloro-5-(p-chlorobenzyloxy)phenyl]-teraconimide,
N-[4-chloro-5-(1-methoxycarbonylethyloxy)phenyl]-teraconimide,
N-[4-chloro-5-(1-ethoxycarbonylethyloxy)phenyl]-teraconimide,
N-(4-chloro-5-methoxycarbonylmethyloxyphenyl)-teraconimide,
N-(4-chloro-5-ethoxycarbonylmethyloxyphenyl)-teraconimide,
N-(4-chloro-5-methylcarbonylmethyloxyphenyl)-teraconimide,
N-(4-chloro-5-phenylcarbonylmethyloxyphenyl)-teraconimide,
N-(4-chloro-5-n-amyloxyphenyl)teraconimide,
N-(4-chloro-5-isoamyloxyphenyl)teraconimide,
N-[4-dichloro-5-(1-methoxy-1-methoxycarbonylmethyloxy)phenyl]-teraconimide,
N-(4-chloro-5-propargyloxyphenyl)teraconimide,
N-(4-chloro-5-cyclopropyloxyphenyl)teraconimide,
N-(4-chloro-5-cyclopentyloxyphenyl)teraconimide,
N-(2-fluoro-4-chloro-5-hydroxyphenyl)teraconimide,
N-(2-fluoro-4-chloro-5-methoxyphenyl)teraconimide,
N-(2-fluoro-4-chloro-5-ethoxyphenyl)teraconimide,
N-(2-fluoro-4-chloro-5-n-propoxyphenyl)teraconimide,
N-(2-fluoro-4-chloro-5-n-butoxyphenyl)teraconimide,
N-(2-fluoro-4-chloro-5-isopropoxyphenyl)teraconimide,
N-(2-fluoro-4-chloro-5-isobutoxyphenyl)teraconimide, N-(2-fluoro-4-chloro-5-sec-butoxyphenyl)teraconimide,
N-(2-fluoro-4-chloro-5-allyloxyphenyl)teraconimide,
N-(2-fluoro-4-chloro-5-crotyloxyphenyl)teraconimide,
N-(2-fluoro-4-chloro-5-methallyloxyphenyl)teraconimide,
N-[2-fluoro-4-chloro-5-(1-methylallyloxy)phenyl]-teraconimide,
N-(2-fluoro-4-chloro-5-propargyloxyphenyl)-teraconimide,
N-(2-fluoro-4-chloro-5-cyclopropyloxyphenyl)-teraconimide,
N-(2-fluoro-4-chloro-5-cyclopentyloxyphenyl)-teraconimide,
N-(2-fluoro-4-chloro-5-cyclohexyloxyphenyl)-teraconimide,
N-[2-fluoro-4-chloro-5-(2-fluoroethyloxy)phenyl]-teraconimide,
N-[2-fluoro-4-chloro-5-(2-chloroethyloxy)phenyl]-teraconimide,
N-[2-fluoro-4-chloro-5-(2-bromoethyloxy)phenyl]-teraconimide,
N-[2-fluoro-4-chloro-5-(2,2,2-trifluoroethyloxy)-phenyl]-teraconimide,
N-(2-fluoro-4-chloro-5-trifluoromethyloxyphenyl)-teraconimide,
N-(2-fluoro-4-chloro-5-difluoromethyloxyphenyl)-teraconimide,
N-[2-fluoro-4-chloro-5-(2-cyanoethyloxy)phenyl]-teraconimide,
N-[2-fluoro-4-chloro-5-(1-cyanoethyloxy)phenyl]-teraconimide,
N-(2-fluoro-4-chloro-5-cyanomethyloxyphenyl)-teraconimide,
N-[2-fluoro-4-chloro-5-(2-hydroxyethyloxy)phenyl]-teraconimide,
N-[2-fluoro-4-chloro-5-(2-methoxyethyloxy)phenyl]-teraconimide,
N-[2-fluoro-4-chloro-5-(2-ethoxyethyloxy)phenyl]-teraconimide,
N-[2-fluoro-4-chloro-5-(2-isopropoxyethyloxy)-phenyl]teraconimide,
N-[2-fluoro-4-chloro-5-(2,3-epoxypropyloxy)-phenyl]teraconimide,
N-[2-fluoro-4-chloro-5-(α-methylbenzyloxy)phenyl]-teraconimide,
N-(2-fluoro-4-chloro-5-benzyloxyphenyl)teraconimide,
N-(2-fluoro-4-chloro-5-phenethyloxyphenyl)-teraconimide,
N-[2-fluoro-4-chloro-5-(p-chlorobenzyloxy)phenyl]-teraconimide,
N-[2-fluoro-4-chloro-5-(1-methoxycarbonylethyloxy)phenyl]teraconimide,
N-[2-fluoro-4-chloro-5-(1-ethoxycarbonylethyloxy)-phenyl]teraconimide,
N-(2-fluoro-4-chloro-5-methoxycarboxylmethyloxyphenyl)teraconimide,
N-(2-fluoro-4-chloro-5-ethoxycarbonylmethyloxyphenyl)teraconimide,
N-(2-fluoro-4-chloro-5-methylcarbonylmethyloxyphenyl)teraconimide,
N-(2-fluoro-4-chloro-5-phenylcarbonylmethyloxyphenyl)teraconimide,
N-(2-fluoro-4-chloro-5-n-amyloxyphenyl)teraconimide,
N-(2-fluoro-4-chloro-5-isoamyloxyphenyl)teraconimide,
N-[2-fluoro-4-chloro-5-(1-methoxy-1-methoxycarbonylmethyloxy)phenyl]teraconimide,
N-(2-fluoro-4-chloro-5-methoxymethoxyphenyl)-teraconimide,
N-[5-[1-(methylcarbamoyl)ethylamino]-2,4-dichlorophenyl]teraconimide,
N-[5-[1-(methylcarbamoyl)ethylamino]-4-chlorophenyl]teraconimide,
N-[1-[1-(methylcarbamoyl)ethylamino]-2-fluoro-4-chlorophenyl]teraconimide,
N-[5-[1-(ethylcarbamoyl)ethylamino]-2,4-dichlorophenyl]teraconimide,
N-[5-[1-(ethylcarbamoyl)ethylamino]-4-chlorophenyl]teraconimide,
N-[5-[1-(ethylcarbamoyl)ethylamino]-2-fluoro-4-chlorophenyl]teraconimide,
N-[5-[1-(n-propylcarbamoyl)ethylamino]-2,4-dichlorophenyl]teraconimide,
N-[5-[1-(n-propylcarbamoyl)ethylamino]-4-chlorophenyl]teraconimide,
N-[5-[1-(n-propylcarbamoyl)ethylamino]-2-fluoro-4chlorophenyl]teraconimide,
N-[5-[1-(iso-propylcarbamoyl)ethylamino]-2,4-dichlorophenyl]teraconimide,
N-[5-[1-(iso-propylcarbamoyl)ethylamino]-4-chlorophenyl]teraconimide,
N-[5-[1-(iso-propylcarbamoyl)ethylamino]-2-fluoro-4chlorophenyl]teraconimide,
N-[5-[1-(n-butylcarbamoyl)ethylamino]-2,4-dichlorophenyl]teraconimide,
N-[5-[1-(n-butylcarbamoyl)ethylamino]-4-chloro phenyl]teraconimide,
N-[5-[1-(n-butylcarbamoyl)ethylamino]-2-fluoro-4-chlorophenyl]teraconimide,
N-[5-[1-(sec-butylcarbamoyl)ethylamino]-2,4-dichlorophenyl]teraconimide,
N-[5-[1-(sec-butylcarbamoyl)ethylamino]-4-chlorophenyl]teraconimide,
N-[5-[1-(sec-butylcarbamoyl)ethylamino]-2-fluoro-4chlorophenyl]teraconimide,
N-[5-[1-(iso-butylcarbamoyl)ethylamino]-2,4-dichlorophenyl]teraconimide,
N-[5-[1-(iso-butylcarbamoyl)ethylamino]-4-chlorophenyl]teraconimide,
N-[5-[1-(iso-butylcarbamoyl)ethylamino]-2-fluoro-4chlorophenyl]teraconimide,
N-[5-[1-(tert-butylcarbamoyl)ethylamino]-2,4-dichlorophenyl]teraconimide,
N-[5-[1-(tert-butylcarbamoyl)ethylamino]-4-chlorophenyl]teraconimide,
N-[5-[1-(tert-butylcarbamoyl)ethylamino]-2-fluoro-4chlorophenyl]teraconimide,
N-[5-[1-(n-amylcarbamoyl)ethylamino]-2,4-dichlorophenyl]teraconimide,
N-[5-[1-(n-amylcarbamoyl)ethylamino]-4-chlorophenyl]teraconimide,
N-[5-[1-(n-amylcarbamoyl)ethylamino]-2-fluoro-4chlorophenyl]teraconimide,
N-[5-[1-(iso-amylcarbamoyl)ethylamino]-2,4-dichlorophenyl]teraconimide,
N-[5-[1-(iso-amylcarbamoyl)ethylamino]-4-chlorophenyl]teraconimide,
N-[5-[1-(iso-amylcarbamoyl)ethylamino]-2-fluoro-4-chlorophenyl]teraconimide,
N-[5-[1-(cyclopropylcarbamoyl)ethylamino]-2,4-dichlorophenyl]teraconimide, N-[5-[1-(cyclopropylcarbamoyl)ethylamino]-4-chlorophenyl]teraconimide,
N-[5-[1-(cyclopropylcarbamoyl)ethylamino]-2-fluoro-4-chlorophenyl]teraconimide,
N-[5-[1-(cyclobutylcarbamoyl)ethylamino]-2,4-dichlorophenyl]teraconimide,
N-[5-[1-(cyclobutylcarbamoyl)ethylamino]-4-chlorophenyl]teraconimide,
N-[5-[1-(cyclobutylcarbamoyl)ethylamino]-2-fluoro-4-chlorophenyl]teraconimide,
N-[5-[1-(cyclopentylcarbamoyl)ethylamino]-2,4-dichlorophenyl]teraconimide,
N-[5-[1-(cyclopentylcarbamoyl)ethylamino]-4-chlorophenyl]teraconimide,
N-[5-[1-(cyclopentylcarbamoyl)ethylamino]-2-fluoro-4chlorophenyl]teraconimide,
N-[5-[1-(cyclohexylcarbamoyl)ethylamino]-2,4-dichlorophenyl]teraconimide,
N-[5-[1-(cyclohexylcarbamoyl)ethylamino]-4-chlorophenyl]teraconimide,
N-[5-[1-(cyclohexylcarbamoyl)ethylamino]-2-fluoro-4-chlorophenyl]teraconimide,
N-[5-[1-(allylcarbamoyl)ethylamino]-2,4-dichlorophenyl]teraconimide,
N-[5-[1-(allylcarbamoyl)ethylamino]-4-chlorophenyl]teraconimide,
N-[5-[1-(allylcarbamoyl)ethylamino]-2-fluoro-4-chlorophenyl]teraconimide,
N-[5-[1-(crotylcarbamoyl)ethylamino]-2,4-dichlorophenyl]teraconimide,
N-[5-[1-(crotylcarbamoyl)ethylamino]-4-chlorophenyl]teraconimide,
N-[5-[1-(crotylcarbamoyl)ethylamino]-2-fluoro-4-chlorophenyl]teraconimide,
N-[5-[1-(propargylcarbamoyl)ethylamino]-2,4-dichlorophenyl]teraconimide,
N-[5-[1-(propargylcarbamoyl)ethylamino]-4-chlorophenyl]teraconimide,
N-[5-[1-(propargylcarbamoyl)ethylamino]-2-fluoro-4chlorophenyl]teraconimide,
N-[5-[1-(1,1-dimethylpropargylcarbamoyl)ethylamino]-2,4-dichlorophenyl]teraconimide,
N-[5-[1-(1,1-dimethylpropargylcarbamoyl)ethylamino]-4-chlorophenyl]teraconimide,
N-[5-[1-(1,1-dimethylpropargylcarbamoyl)ethylamino]-2- fluoro-4-chlorophenyl]teraconimide,
N-[5-[1-(N-methoxy-N-methylcarbamoyl)ethylamino]-2,4-dichlorophenyl]teraconimide,
N-[5-[1-(N-methoxy-N-methylcarbamoyl)ethylamino]-4-chlorophenyl]teraconimide,
N-[5-[1-(N-methoxy-N-methylcarbamoyl)ethylamino]-2-fluoro-4-chlorophenyl]teraconimide,
N-[5-[1-(N-ethoxy-N-ethylcarbamoyl)ethylamino]-2,4-dichlorophenyl]teraconimide,
N-[5-[1-(N-ethoxy-N-ethylcarbamoyl)ethylamino]-4-chlorophenyl]teraconimide,
N-[5-[1-(N-ethoxy-N-ethylcarbamoyl)ethylamino]-2-fluoro-4-chlorophenyl]teraconimide,
N-[5-[1-(N-methoxy-N-ethylcarbamoyl)ethylamino]-2,4-dichlorophenyl]teraconimide,
N-[5-[1-(N-methoxy-N-ethylcarbamoyl)ethylamino]-4-chlorophenyl]teraconimide,
N-[5-[1-(N-methoxy-N-ethylcarbamoyl)ethylamino]-2-fluoro-4-chlorophenyl]teraconimide,
N-[5-[1-(N-propoxy-N-propylcarbamoyl)ethylamino]-2-fluoro-4-chlorophenyl]teraconimide,
N-[5-[1-(N,N-dimethylcarbamoyl)ethylamino]-2,4-dichlorophenyl]teraconimide,
N-[5-[1-(N,N-dimethylcarbamoyl)ethylamino]-4-chlorophenyl]teraconimide,
N-[5-[1-(N,N-dimethylcarbamoyl)ethylamino]-2-fluoro-4-chlorophenyl]teraconimide,
N-[5-[1-(N,N-diethylcarbamoyl)ethylamino]-2,4-dichlorophenyl]teraconimide,
N-[5-[1-(N,N-diethylcarbamoyl)ethylamino]-4-chlorophenyl]teraconimide,
N-[5-[1-(N,N-diethylcarbamoyl)ethylamino]-2,4-dichlorophenyl]teraconimide,
N-[5-[1-(N,N-diethylcarbamoyl)ethylamino]-4-chlorophenyl]teraconimide,
N-[5-[1-(N,N-diethylcarbamoyl)ethylamino]-2-fluoro-4-chlorophenyl]teraconimide,
N-[5-[1-(N,N-diallylcarbamoyl)ethylamino]-2,4-dichlorophenyl]teraconimide,
N-[5-[1-(N,N-diallylcarbamoyl)ethylamino]-4-chlorophenyl]teraconimide,
N-[5-[1-(N,N-diallylcarbamoyl)ethylamino]-2-fluoro-4-chlorophenyl]teraconimide,
N-[5-[1-(N,N-diisopropylcarbamoyl)ethylamino]-4-chlorophenyl]teraconimide,
N-[5-[1-(N,N-diisopropylcarbamoyl)ethylamino]-2-fluoro-4-chlorophenyl]teraconimide,
N-[5-[1-(morpholinocarbamoyl)ethylamino]-2,4-dichlorophenyl]teraconimide,
N-[5-[1-(morpholinocarbamoyl)ethylamino]-4-chlorophenyl]teraconimide,
N-[5-[1-(morpholinocarbamoyl)ethylamino]-2-fluoro-4-chlorophenyl]teraconimide,
N-[5-[1-(piperidinocarbamoyl)ethylamino]-2,4-dichlorophenyl]teraconimide,
N-[5-[1-(piperidinocarbamoyl)ethylamino]-4-chlorophenyl]teraconimide,
N-[5-[1-(piperidinocarbamoyl)ethylamino]-2-fluoro-4-chlorophenyl]teraconimide,
N-[5-[1-(methoxyethylcarbamoyl)ethylamino]-2,4-dichlorophenyl]teraconimide,
N-[5-[1-(methoxyethylcarbamoyl)ethylamino]-4-chlorophenyl]teraconimide,
N-[5-[1-(methoxyethylcarbamoyl)ethylamino]-2-fluoro-4-chlorophenyl]teraconimide,
N-[5-[1-(ethoxyethylcarbamoyl)ethylamino]-4-chlorophenyl]teraconimide,
N-[5-[1-(ethoxyethylcarbamoyl)ethylamino]-2-fluoro-4-chlorophenyl]teraconimide,
N-[5-[1-(N-methoxycarbamoyl)ethylamino]-4-chlorophenyl]teraconimide,
N-[5-[1-(N-methoxycarbamoyl)ethylamino]-2-fluoro-4-chlorophenyl]teraconimide,
N-[5-[1-(N-ethoxycarbamoyl)ethylamino]-4-chlorophenyl]teraconimide,
N-[5-[1-(N-ethoxycarbamoyl)ethylamino]-2-fluoro-4-chlorophenyl]teraconimide,
N-[5-[1-(N-iso-propoxycarbamoyl)ethylamino]-4-chlorophenyl]teraconimide,
N-[5-[1-(N-iso-propoxycarbamoyl)ethylamino]-2-fluoro4-chlorophenyl]teraconimide,
N-[5-[1-(N-n-butoxycarbamoyl)ethylamino]-4-chlorophenyl]teraconimide,
N-[5-[1-(N-n-butoxycarbamoyl)ethylamino]-2-fluoro-4-chlorophenyl]teraconimide,
N-[5-[1-(ethoxycarbonylmethylcarbamoyl)ethylamino]-4-chlorophenyl]teraconimide,
N-[5-[1-(ethoxycarbonylmethylcarbamoyl)ethylamino]-2-fluoro-4-chlorophenyl]teraconimide,
N-[5-[1-(iso-butylcarbamoyl)methylamino]-4-chlorophenyl]teraconimide, N-[5-[1-(iso-butylcarbamoyl)methylamino]-2-fluoro-4-chlorophenyl]teraconimide, N-[5-[1-(morpholinocarbamoyl)methylamino]-4-chlorophenyl]teraconimide, N-[5-[1-(morpholinocarbamoyl)methylamino]-2-fluoro-4-chlorophenyl]teraconimide, N-[5-[1-(iso-butylcarbamoyl)propylamino]-4-chlorophenyl]teraconimide, N-[5-[1-(iso-butylcarbamoyl)propylamino]-2-fluoro-4-chlorophenyl]teraconimide, N-[5-[1-(morpholinocarbamoyl)propylamino]-4-chlorophenyl]teraconimide, N-[5-[1-(morpholinocarbamoyl)propylamino]-2-fluoro-4-chlorophenyl]teraconimide, N-[5-[1-(iso-butylcarbamoyl)butylamino]-2-fluoro-4-chlorophenyl]teraconimide, N-[5-[1-(morpholinocarbamoyl)butylamino]-2-fluoro-4-chlorophenyl]teraconimide, N-[5-[1-(cyclohexylcarbamoyl)butylamino]-2-fluoro-4-chlorophenyl]teraconimide, N-[5-[1-(hydroxyethylcarbamoyl)ethylamino]-4-chlorophenyl]teraconimide, N-[5-[1-(hydroxyethylcarbamoyl)ethylamino]-2-fluoro-4-chlorophenyl]teraconimide, N-[5-[1-(cyanomethylcarbamoyl)ethylamino]-4-chlorophenyl]teraconimide, N-[5-[1-(cyanomethylcarbamoyl)ethylamino]-2-fluoro-4-chlorophenyl]teraconimide, N-[5-[1-(2-cyanoethylcarbamoyl)ethylamino]-4-chlorophenyl]teraconimide, N-[5-[1-(2-cyanoethylcarbamoyl)ethylamino]-2-fluoro-4-chlorophenyl]teraconimide, N-[5-[1-(phenylcarbamoyl)ethylamino]-4-chlorophenyl]teraconimide, N-[5-[1-(phenylcarbamoyl)ethylamino]-2-fluoro-4-chlorophenyl]teraconimide, N-[5-[1-(benzylcarbamoyl)ethylamino]-4-chlorophenyl]teraconimide, N-[5-[1-(benzylcarbamoyl)ethylamino]-2-fluoro-4-chlorophenyl]teraconimide, N-[5-[1-(N-ethyl-N-n-propylcarbamoyl)ethylamino]-2-fluoro-4-chlorophenyl]-teraconimide, N-[5-[1-(N-ethyl-N-n-propylcarbamoyl)ethylamino]-4-chlorophenyl]-teraconimide, N-[5-[1-(N-methoxy-N-methylcarbamoyl)-propylamino]-2-fluoro-4-chlorophenyl]-teraconimide and N-[5-[1-(N-methoxy-N-methylcarbamoyl)-propylamino]-4-chlorophenyl]-teraconimide.

All of the above compounds are novel compounds which have not been disclosed in the literature. They may be prepared according to, for example, Method A to Method C, as described below.

Method A

Reaction process:

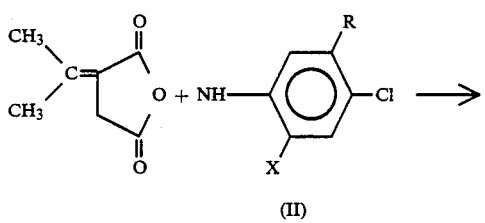

(II)

-continued
Reaction process:

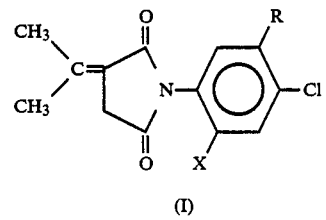

(I)

wherein X and R are as defined hereinbelow.

In this method, a substituted aniline represented by the formula (II) is reacted with teraconic acid anhydride either in the absence of a solvent or in the presence of an inert solvent having a high boiling point such as acetic acid, o-dichlorobenzene and the like at a temperature of from about 100° to 200° C., preferably from about 120° to 170° C., for about 2 to 10 hours to obtain a compound represented by the formula II) according to the present invention. The molar ratio of the compound (II) to teraconic acid anhydride is preferably about 1.

This process, which involves two reactions, i.e. formation of an amide and dehydration-ring closure to an imide, may also be effected by other conditions. That is, the first step of amidation is conducted under moderate conditions, i.e. at a temperature of from room temperature to about 100° C., in the presence of a solvent. Then, the solvent is removed and the second step of dehydration-ring closure is conducted using a dehydrating agent under the moderate conditions to form an imide. The molar ratio of the dehydrating agent to the amide is preferably in the range of from about 1:1 to 2:1. Suitable solvents to be used in the above first step include ether type solvents such as tetrahydrofuran, dioxane; aromatic solvents such as toluene; halogenated hydrocarbon type solvents such as chloroform; and aprotic polar solvents such as N,N-dimethylformamide, dimethylsulfoxide. The dehydrating agent to be used in the above second process includes acetic acid anhydride/sodium acetate, thionyl chloride and the like.

Method B

Reaction process:

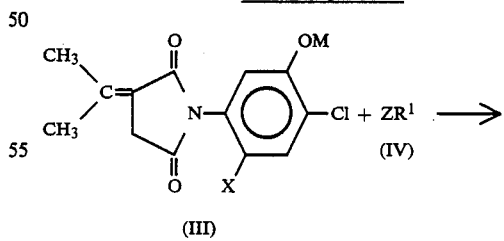

(III)

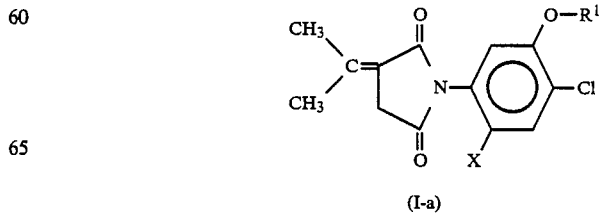

(I-a)

wherein X and $R^1$ are as defined hereinbefore, Z represents a halogen atom and M represents an alkali metal atom.

In this method, an N-substituted-phenylteraconimide compound represented by the formula (III) is reacted with a halide represented by the formula (IV) in a solvent such as acetonitrile, dimethylformamide, dimethylacetamide, dimethylsulfoxide and the like at a temperature of from room temperature to 100° C., preferably from 50° to 80° C., for about 2 to 10 hours to obtain a compound represented by the formula (I-a) according to the present invention. The molar ratio of the compound (III) to the compound (IV) is preferably in the range of from about 1:1 to 1:1.5.

Besides the above-mentioned solvents, there may also preferably be employed tetrahydrofuran in which 18-crown-6 is contained as a phase-transfer catalyst.

Method C

Reaction process:

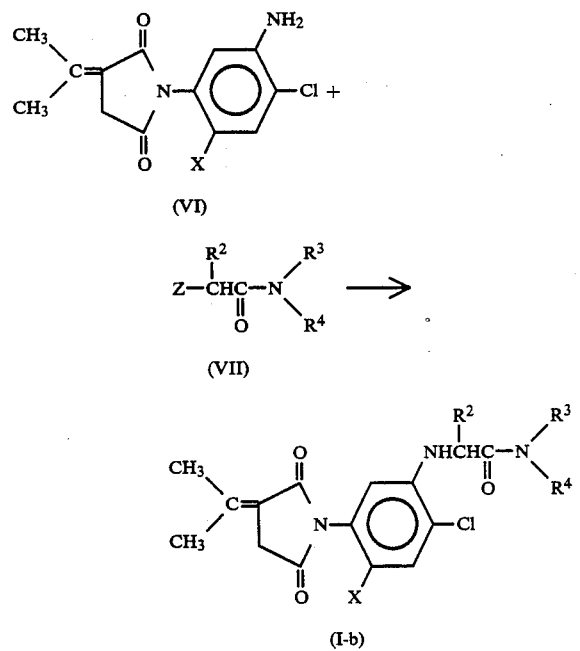

wherein X, $R^2$, $R^3$, $R^4$ and Z are as defined hereinbefore.

In this method, an aniline derivative represented by the formula (VI) is reacted with a carboxamide derivative represented by the formula (VII) at a temperature of from 50° to 250° C. for about 2 to 10 hours to obtain a compound represented by the formula (I-b) according to the present invention. The molar ratio of the compound (VI) to the compound (VII) is preferably 1. This reaction is conducted either in a solvent or not in a solvent, in the presence of a basic compound such as sodium bicarbonate, potassium bicarbonate, sodium carbonate, potassium carbonate, sodium acetate, sodium hydroxide and the like, and either in the absence or in the presence of an iodide such as sodium iodide, potassium iodide and the like. As the solvent to be used in this method, there may be mentioned o-dichlorobenzene, dimethylsulfoxide, sulfolane, N,N-dimethylformamide, benzene, toluene, acetone, 2-butanone, tetrahydrofuran, acetonitrile, dioxane or the like.

The above Methods A to C are illustrative of preferred processes for producing the compounds of the present invention. It should be understood that these methods are not intended to limit the process for producing the compound of the present invention. The compounds of the present invention may be produced by various methods which are modifications of conventionally known methods for producing similar compounds.

The herbicidal activity of the compound of the present invention is illustrated hereinbelow with respect to the prevention and elimination of weeds which grow on paddy fields. The compound of the present invention can be effectively applied to paddy fields for a prolonged period of time including the pre-transplantaiton and post-transplantation periods of rice plant seedlings. Especially, the compound is useful to effectively and promptly destroy annual weeds in paddy fields. Moreover, the compound of the present invention has no significant phytotoxicity to rice plants when it is applied in such an effective amount that the weeds are destroyed effectively. Further, the compound of the present invention also exhibits high herbicidal activities to perennial weeds on paddy fields, such as "Hotarui" (Scirpus juncoides), flat sedge and the like.

The compound of the present invention exhibits extremely high herbicidal activities not only to the paddy field weeds but also to the upland weeds. The compound of the present invention exhibits high herbicidal activities even in a small dosage to a variety of weeds, for example, broad-leaved weeds such as livid amaranth, smartweed, cocklebur, common chickweed, bind weed and the like, and the weeds belonging to the family Gramineae such as crabgrass, goosegrass, green foxtail, annual poa and the like. The characteristic feature of the compound of the present invention resides in that the compound exhibits, in both of the preemergence and postemergence applications, an excellent selectivity for not only broad-leaved crop plants such as soybean, cotton and the like but also crop plants belonging to the family Gramineae such as rice, corn, wheat plants and the like. Further, due to its wide applicability and excellent herbicidal activities, the compound of the present invention is also useful as an effective herbicide for a pasture, an orchard, a lawn and a noncropland.

In practical application of the present compound as a herbicide, it may be applied as such, or may be formulated into various types of preparations, such as wettable powder, emulsifiable concentrate, granule, dust and the like.

Hence, in another aspect of the present invention, there is provided a herbicidal composition which comprises as an active ingredient a herbicidally effective amount of a compound represented by the formula

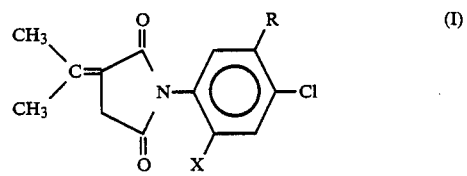

wherein R and X are as defined above.

The term "a herbicidally effective amount" used herein is intended to mean an amount required under the environmental conditions in order to effectively control weeds, that is, the weeds are severely injured so as not to be able to recover from the application of the compound or are killed, and no substantial injury is caused to the crops.

As the solid carrier to be used for formulating the present compound into the above-described various preparations, there may be mentioned mineral powder (e.g. kaolin, bentonite, clay, montmorillonite, talc, diatomite, mica, vermiculite, gypsum, calcium carbonate, apatite and the like), vegetable powder (e.g. soybean meal, wheat flour, wood meal, tobacco powder, starch, crystalline cellulose and the like), high polymer compounds (e.g. petroleum resin, polyvinyl chloride, ketone resin and the like) and, further, alumina and waxes.

As the liquid carrier, there may be mentioned, for example, alcohols (methanol, ethanol, butanol, ethylene glycol, benzyl alcohol and the like), aromatic hydrocarbons (such as toluene, benzene, xylene and the like), chlorinated hydrocarbons (chloroform, carbon tetrachloride, monochlorobenzene and the like), ethers (dioxane, tetrahydrofuran and the like), ketones (acetone, methyl ethyl ketone, cyclohexanone and the like), esters (ethyl acetate, butyl acetate and the like), acid amids (N,N-dimethylacetamide and the like), nitriles (acetonitrile and the like), ether alcohols (ethylene glycol ethyl ether and the like) and water.

As the surface active agent to be used to effect emulsifying, dispersing, spreading and the like for the present compound, there may be mentioned nonionic, anionic, cationic and amphoteric ones. Specific examples of the surface active agent which can be employed in the present invention are a polyoxyethylene alkyl ether, a polyoxyethylene alkylaryl ether, a polyoxyethylene fatty acid ester, a sorbitan fatty acid ester, a polyoxyethylene sorbitan fatty acid ester, an oxyethylene polymer, an oxypropylene polymer, a polyoxyethylene alkyl phosphate, a fatty acid salt, an alkyl sulfate salt, an alkyl sulfonate salt, an alkyl aryl sulfonate salt, an alkyl phosphate salt, a polyoxyethylene alkyl sulfate, a quaternary ammonium salt and an oxyalkylamine. The surface active agent which can be used in the present invention is by no means limited to the above surface active agents. Further, according to need, gelatin, casein, sodium alginate, starch, agar, polyvinyl alcohol and the like may be used as an auxiliary additive in the present invention.

The content of the compound (I) of the present invention in the herbicidal composition may vary depending on the type of the composition and the purpose for which the composition is designed. The amount, however, is generally from about 0.05 to 95% by weight, preferably about 5 to 75% by weight based on the total weight of the composition.

Moreover, in order to improve its effects as a herbicide, the compound of the present invention may be mixed with other herbicidally active ingredients and, in some cases, a synergistic effect is expected. For example, the following ingredients may be mixed with the compound of the present invention:

(A) Phenoxy type herbicide 2,4-dichlorophenoxyacetic acid; 2-methyl-4-chlorophenoxyacetic acid; butyl 2-[4-(5-trifluoromethyl-2-pyridyloxy)phenoxy]propionate (including esters and salts thereof); ethyl 2-[4-(6-chloro-2-quinoxalinyloxy)-phenoxy]propionate; etc.

(B) Diphenyl ether type herbicide 2,4-dichlorophenyl-4'-nitrophenyl ether; 2,4,6-trichlorophenyl 4'-nitrophenyl ether; 2,4-dichlorophenyl 4'-nitro-3'-methoxyphenyl ether; 2,4-dichlorophenyl 3'-methoxycarbonyl-4'-nitrophenyl ether; 2-chloro-4-trifluoromethylphenyl 3'-ethoxy-4'-nitrophenyl ether; sodium 5-[2-chloro-4-(trifluoromethyl)phenoxy]-2-nitrobenzoate; etc.

(C) Triazine type herbicide 2-chloro-4,6-bis-ethylamino-1,3,5-triazine; 2-chloro-4-ethylamino-6-isopropylamino-1,3,5-triazine; 2-methylthio-4,6-bis-ethylamino-1,3,5-triazine; etc.

(D) Urea type herbicide 3-(3,4-dichlorophenyl)-1,1-dimethylurea; 3-(3,4-dichlorophenyl)-1-methoxy-1-methylurea; 3-($\alpha,\alpha,\alpha$-trifluoro-m-tolyl)-1,1-dimethylurea; 3-[4-(4-methylphenethyloxy)phenyl]-1-methoxy-1-methylurea; 3-(5-t-butyl-3,4-thiadiazol-2-yl)-4-hydroxy-1-methyl-2-imidazolidone; etc.

(E) Carbamate type herbicide isopropyl N-(3-chlorophenyl)carbamate; methyl N-(3,4-dichlorophenyl)carbamate; 4-chloro-2-butynyl N-(3-chlorophenyl)carbamate; etc.

(F) Thiolcarbamate type herbicide

S-ethyl N,N-hexamethylenethiolcarbamate; S-(4-chlorobenzyl) N,N-diethylthiolcarbamate; S-ethyl dipropylthiolcarbamate; etc.

(G) Anilide type herbicide 3,4-dichloropropionanilide; N-methoxymethyl-2',6'-diethyl-2-chloroacetanilide; 2-chloro-2',6'-diethyl-N-(butoxymethyl)acetanilide; 2-chloro-2',6'-diethyl-N-(propoxyethyl)acetanilide; $\alpha$-(2-naphthoxy)propionanilide; etc.

(H) Uracil type herbicide 5-bromo-3-sec-butyl-6-methyluracil; 3-cyclohexyl-5,6-trimethyleneuracil; etc.

(I) Dipyridinium salt type herbicide 1,1'-dimethyl-4,4'-dipyridinium dichloride; 1,1'-ethylene-2,2'-dipyridinium dibromide; etc.

(J) Phosphorus type herbicide

N-(phosphonomethyl)glycine; O-ethyl-O-(2-nitro-5-methylphenyl)-N-sec-butylphosphoroamidothioate; O-methyl-O-(2-nitro-4-methylphenyl)-N-isopropylphosphoroamidothioate; S-(2-methyl-1,1-piperidylcarbonylmethyl)-O,O-di-n-propyl dithiophosphate; (2-amino-4-methylphosphinobutyryl)alanylalanine monosodium salt; etc.

(K) Toluidine type herbicide $\alpha,\alpha,\alpha$-trifluoro-2,6-dinitro-N,N-dipropyl-p-toluidine; N-(cyclopropylmethyl)-$\alpha,\alpha,\alpha$-trifluoro-2,6-dinitro-N-propyl-p-toluidine; etc.

(L) Other herbicides 5-t-butyl-3-(2,4-dichloro-5-isopropoxyphenyl)-1,3,4-oxadiazolin-2-one; 3-isopropyl-2,1,3-benzothiaziadinone-4,2,2-dioxide; 2-($\alpha$-naphthoxy)-N,N-diethylpropionamide; 3-amino-2,5-dichlorobenzoic acid; 4-(2,4-dichlorobenzoyl)-1,3-dimethylpyrazol-5-yl-p-toluene sulfonate; 2-chloro-N-[(4-methoxy-6-methyl-1,3,5-triazine-2-yl)aminocarbonyl]benzenesulfonamide; methyl 2-[(4,6-dimethoxypyrimidin-2-yl)aminocarbonylaminosulfonylmethyl]benzoate; N-(1-methyl-1- phenylethyl)-2-bromo-3,3-dimethylbutanamide; 2-[1-(N-allyloxyamino)butylidene]-4-methoxycarbonyl-5,5-dimethylcyclohexane-1,3-dione sodium salt; 2-[1-(ethoxyimino)butyl]-5-(2-ethylthiopropyl)-3-hydroxy-2-cyclohexan-1-one; etc.

The foregoing herbicides are mentioned only as the examples, and they should not be construed to be limiting the scope of herbicides which can be utilized in combination with the compound of the present invention. The herbicide of the present invention may also be applied in combination with insecticides such as pyrethroid type insecticides and the like, fungicides, plant growth regulators, microbial agricultural chemicals and fertilizers.

In a further aspect of the present invention, there is provided a method for the destruction of undesirable weeds, which comprises applying to the weeds, in an amount of from 0.4 to 100 g/10a in terms of the amount of an active ingredient, a herbicidal composition which comprises as an active ingredient a herbicidally effective amount of an N-substituted-phenylteraconimide compound represented by the formula

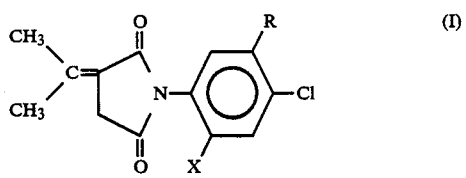

wherein R and X are as defined above.

The above-described method is useful in selectively and effectively controlling undesirable weeds among desirable crop plants. Further, the method is continuously useful through the whole period of growth of crop plants including broad-leaved crop plants such as soybean, cotton and the like and crop plants belonging to the family Gramineae such as rice, corn and wheat plants.

In Application Examples which will be given later and in which the active compound is applied in the form of a herbicidal composition, the dosage of the composition is expressed using the unit "a.i. g/10a" which means "g/10a in terms of the amount of an active ingredient".

The present invention will now be explained in more detail with reference to Synthesis Examples with respect to the synthesis of the compounds of the present invention, Preparation Examples with respect to the recipes for the herbicidal compositions and Application Examples with respect to effectiveness of the herbicidal compositions of the present invention. These Examples are not to be construed as limiting the scope of the present invention in any manner.

SYNTHESIS EXAMPLE

EXAMPLE 1

Synthesis of N-(2-fluoro-4-chloro-5-hydroxyphenyl)-teraconimide: Compound No. 69

11 g of teraconic acid anhydride and 13 g of 2-chloro-4-fluoro-5-aminophenol were dissolved in 250 ml of acetic acid and the solution was heated under reflux at about 130° to 140° C. for 5 hours. After completion of the reaction, the acetic acid was distilled off under reduced pressure to obtain a crude product. The thus obtained crude product was subjected to purification by the column chromatography using a mixture of toluene and acetone as the eluent, thereby to obtain 17 g of a yellow viscous liquid of N-(2-fluoro-4-chloro-5-hydroxyphenyl)teraconimide.

EXAMPLE 2

Synethesis of N-(2-fluoro-4-chloro-5-propargyloxyphenyl)teraconimide: Compound No. 71

1.5 g of a potassium salt of N-(2-fluoro-4-chloro-5-hydroxyphenyl)teraconimide and 0.6 g of propargyl bromide were dissolved in 20 ml of tetrahydrofuran. To the solution was added 0.1 g of 18-crown-6, followed by stirring at 40° to 50° C. for 3 hours. After completion of the reaction, the tetrahydrofuran was distilled off under reduced pressure to obtain a crude product. The thus obtained crude product was subjected to purification by the column chromatography using a mixture of toluene and acetone as the eluent, thereby to obtain 0.7 g of a light yellow crystalline substance of N-(2-fluoro-4-chloro-5-propargyloxyphenyl)teraconimide having a melting point of 134.7° to 135.5° C.

EXAMPLE 3

Synthesis of N-(4-chloro-5-hydroxyphenyl)teraconimide: Compound No. 49

11 g of teraconic acid anhydride and 11 g of 2-chloro-5-aminophenol were dissolved in 250 ml of acetic acid and the solution was heated under reflux at about 130° to 140° C. for 5 hours. After completion of the reaction, the acetic acid was distilled off to obtain a crude product. The thus obtained crude product was subjected to purification by the column chromatography using a mixture of toluene and acetone as the eluent, thereby to obtain 14 g of a light yellow crystalline substance of N-(4-chloro-5-hydroxyphenyl)teraconimide having a melting point of 164.8° to 165.7° C.

EXAMPLE 4

Synthesis of N-(4-chloro-5-propargyloxyphenyl)-teraconimide: Compound No. 51

1.5 g of a potassium salt of N-(4-chloro-5-hydroxyphenyl)teraconimide and 0.6 g of propargyl bromide were dissolved in 20 ml of tetrahydrofuran. To the solution was added 0.1 g of 18-crown-6, followed by stirring at 40° to 50° C. for 3 hours. After completion of the reaction, the tetrahydrofuran was distilled off under reduced pressure to obtain a crude product. The thus obtained crude product was subjected to purification by the column chromatography using a mixture of toluene and acetone as the eluent, thereby to obtain 0.7 g of a light yellow crystalline substance of N-(4-chloro-5-propargyloxyphenyl)teraconimide having a melting point of 161.5° to 162.2° C.

EXAMPLE 5

Synthesis of N-(2,4-dichloro-5-hydroxyphenyl)-teraconimide: Compound No. 9

11 g of teraconic acid anhydride and 14 g of 2,4-dichloro-5-aminophenol were dissolved in 250 ml of acetic acid. The solution was heated under reflux at about 130° to 140° C. for 5 hours. After completion of the reaction, the acetic acid was distilled off under reduced pressure to obtain a crude product. The thus obtained crude product was subjected to purification by the column chromatography using a mixture of toluene and acetone as the eluent, thereby to obtain 13 g of a light yellow crystalline substance of N-(2,4-dichloro-5- hydroxyphenyl)teraconimide having a melting point of 157.0° to 157.3° C.

EXAMPLE 6

Synthesis of N-(2,4-dichloro-5-propargyloxyphenyl)-teraconimide: Compound No. 11

1.5 g of a potassium salt of N-(2,4-dichloro-5-hydroxyphenyl)teraconimide and 0.6 g of propargyl bromide were dissolved in 20 ml of tetrahydrofuran. To the solution was added 0.1 g of 18-crown-6, followed by stirring at 40° to 50° C. for 3 hours. After completion of the reaction, the tetrahydrofuran was distilled off under reduced pressure to obtain a crude product. The thus obtained crude product was subjected to purification by the column chromatography using a mixture of toluene and acetone as the eluent, thereby to obtain 0.8 g of a light yellow crystalline substance of N-(2,4-dichloro-5-propargyloxyphenyl)teraconimide having a melting point of 128.5° to 129.3° C.

EXAMPLE 7

Synthesis of N-[5-[1-(sec-butylcarbamoyl)ethylamino]-4-chlorophenyl]teraconimide: Compound No. 87

5.3 g of N-(3-amino-4-chlorophenyl)teraconimide, 4.6 g of N-sec-butyl-α-bromopropionamide and 2 g of sodium bicarbonate were mixed and then heated at 160° C. for 3 hours to effect reaction. After completion of the reaction, the resultant mixture was cooled and dissolved in acetone, followed by filtration-removal of the insoluble substances. The acetone in the filtrate was distilled off to obtain a crude product. The thus obtained crude product was subjected to purification by the silica gel column chromatography using a mixture of toluene and acetone as the eluent, thereby to obtain 3.4 g of a yellow crystalline substance of N-[5-[1-(sec-butylcarbamoyl)ethylamino]-4-chlorophenyl]teraconimide having a melting point of 58.5° to 59.5° C.

EXAMPLE 8

Various N-substituted-phenylteraconimide compounds of the present invention were synthesized from respective corresponding starting materials as indicated in Tables 1A to 1D in substantially the same manner as in Examples mentioned above. The physical properties and analytical data of these compounds are as shown in the Tables. In the columns of physical property in the Tables, the term "viscous liquid" means that the prepared compounds were viscous liquids at room temperature immediately after synthesis.

The $^1$H-NMR spectral data were obtained by using PMX-60 Si type analyzer (trade name of an $^1$H-NMM analyzer produced by JEOL, Japan).

Thin-layer chromatography (TLC) was effected using, as the silica gel plate, No. 5729 silica gel plate produced by Merck and Co., Inc., U.S.A. and as the eluent, a 8:2 mixture of toluene and acetone.

TABLE 1A

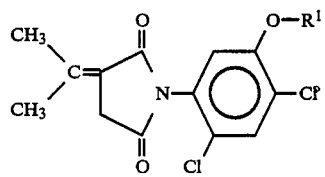

| Compound No. | $R^1$ | Physical property | Elemental analysis (%) Calculated value C | H | N | Found value C | H | N | $^1$H-NMR Spectral Data (δ: CDCl$_3$) |
|---|---|---|---|---|---|---|---|---|---|
| 1 | CH$_3$ | mp (°C.) 119.7–120.7 | 53.52 | 4.17 | 4.45 | 53.63 | 4.10 | 4.32 | 1.90(s,3H), 2.23–2.43(m,3H), 3.23–3.43 (m,2H), 3.78(s,3H), 6.63(s,1H), 7.35(s,1H) |
| 2 | C$_2$H$_5$ | mp (°C.) 108.5–110.5 | 54.89 | 4.60 | 4.26 | 54.85 | 4.69 | 4.28 | 1.42(t,3H), 1.92(s,3H), 2.28–2.47(m,3H), 3.23–3.47(m,2H), 4.00(q,2H), 6.65(s,1H), 7.37(s,1H) |
| 3 | n-C$_4$H$_9$ | Viscous liquid | 57.31 | 5.37 | 3.93 | 54.44 | 5.42 | 3.96 | 0.75–1.85(m,7H), 1.87(s,3H), 2.26–2.45(m, 3H), 3.21–3.45(m,2H), 3.90(t,2H), 6.65(s, 1H), 7.40(s.1H) |
| 4 | n-C$_6$H$_{13}$ | Viscous liquid | 59.38 | 6.03 | 3.64 | 59.31 | 6.09 | 3.60 | 0.66–2.02(m,11H), 1.90(s,3H), 2.23–2.43 (m,3H), 3.28–3.45(m,2H), 3.88(t,2H), 6.66 (s,1H), 7.33(s,1H) |
| 5 | n-C$_8$H$_{17}$ | Viscous liquid | 61.16 | 6.59 | 3.39 | 61.21 | 6.57 | 3.41 | 0.63–1.97(m,15H), 1.90(s,3H), 2.20–2.45 (m,3H, 3.23–3.43(m,2H), 3.90(t,2H), 6.62 (s,1H, 7.33(s,1H) |
| 6 | i-C$_3$H$_7$ | mp (°C.) 100.5–102.2 | 56.15 | 5.00 | 4.09 | 56.08 | 5.07 | 4.03 | 1.35(d,6H), 1.92(s,3H), 2.23–2.43(m,3H), 3.26–3.43(m,2H), 4.45(m,1H), 6.70(s,1H), 7.40(s,1H) |
| 7 | i-C$_4$H$_9$ | mp (°C.) 107.1–107.8 | 57.31 | 5.37 | 3.93 | 57.30 | 5.31 | 3.81 | 1.00(d,6H), 1.90(s,3H), 2.10(m,1H), 2.23–2.45(m,3H), 3.25–3.45(m,2H), 3.68 (d,2H), 6.63(s,1H), 7.40(s,1H) |
| 8 | sec-C$_4$H$_9$ | Viscous liquid | 57.31 | 5.37 | 3.93 | 57.27 | 5.33 | 3.91 | 0.95(t,3H), 1.28(d,3H), 1.66(m,2H), 1.92 (s,3H), 2.20–2.45(m,3H), 3.23–3.45(m,2H), 4.20(m,1H), 6.65(s,1H), 7.40(s,1H) |
| 9 | H | mp (°C.) 157.0–157.3 | 52.02 | 3.69 | 4.66 | 52.00 | 3.74 | 4.58 | 1.90(s,3H), 2.25–2.45(m,3H), 3.23–3.47 (m,2H), 6.50(b,1H), 6.63(s,1H), 7.30(s,1H) |
| 10 | CH$_2$CH=CH$_2$ | Viscous liquid | 56.48 | 4.44 | 4.11 | 56.55 | 4.37 | 4.12 | 1.90(s,3H), 2.20–2.40(m,3H), 3.23–3.40 (m,2H), 4.37–4.53(m,2H), 5.02–6.30(m,3H), 6.60(s,1H), 7.35(s,1H) |
| 11 | CH$_2$C≡CH | mp (°C.) 128.5–129.3 | 56.82 | 3.87 | 4.14 | 56.92 | 3.81 | 4.11 | 1.90(s,3H), 2.20–2.45(m,3H), 2.53(m,1H,) 3.25–3.40(m,2H), 4.63(d,2H), 6.80(s,1H), 7.38(s,1H) |

TABLE 1A-continued

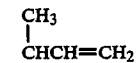

| Compound No. | R¹ | Physical property | Elemental analysis (%) Calculated value C / H / N | Found value C / H / N | $^1$H-NMR Spectral Data (δ: CDCl$_3$) |
|---|---|---|---|---|---|
| 12 | CH₃–CHCH=CH₂ | Viscous liquid | 57.64 4.83 3.95 | 57.68 4.89 3.94 | 1.43(d,3H), 1.90(s,3H), 2.23-2.45(m,3H), 3.20-3.50(m,2H), 4.37-6.17(m,4H), 6.68 (s,1H), 7.42(s,1H) |
| 13 | CH₃–C(=CH₂)CH₂ | mp (°C.) 120.2-120.8 | 57.64 4.83 3.95 | 57.62 4.81 3.97 | 1.80(s,3H), 1.92(s,3H), 2.27-2.45(m,3H), 3.27-3.50(m,2H), 4.40(s,2H), 5.00(d,2H), 6.70(s,1H), 7.43(s,1H) |
| 14 | CH₂CH=CHCH₃ | Viscous liquid | 57.64 4.83 3.95 | 57.69 4.87 3.98 | 1.56-1.80(m,3H), 1.90(s,3H), 2.23-2.42 (m,3H), 3.23-3.43(m,2H), 4.27-4.60(m,2H), 5.52-5.82(m,2H), 6.65(s,1H), 7.40(s,1H) |
| 15 | CH₂CH=C(CH₃)₂ | Viscous liquid | 58.70 5.20 3.80 | 58.71 5.22 3.87 | 1.68(s,3H), 1.78(s,3H), 1.92(s,3H), 2.23-2.43(m,3H), 3.30-3.52(m,2H), 4.40-4.73 (m,2H), 5.12-5.66(m,1H), 6.72(s,1H), 7.43(s,1H) |
| 16 | 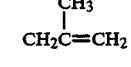 | mp (°C.) 136.4-136.7 | 59.69 5.53 3.66 | 59.62 5.51 3.67 | 1.13-2.07(m,10H), 1.90(s,3H), 2.28-2.40 (m,3H), 3.23-3.43(m,2H), 4.25(m,1H) 6.64(s,1H), 7.40(s,1H) |
| 17 | CH₂CH₂Cl | Viscous liquid | 49.68 3.89 3.86 | 49.59 3.92 3.85 | 1.90(s,3H), 2.20-2.45(m,3H), 3.20-3.43 (m,2H), 3.73(t,2H), 4.15(t,2H), 6.67(s,1H), 7.40(s,4H) |
| 18 | CH₂CH₂OH | Viscous liquid | 52.34 4.39 4.06 | 52.31 4.29 4.12 | 1.92(s,3H), 2.25-2.45(m,3H), 2.40(b,1H), 3.23-3.50(m,2H), 3.73-4.23(m,4H), 6.73 (s,1H), 7.45(s,1H) |
| 19 | 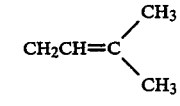 | Viscous liquid | 53.95 4.24 3.93 | 53.91 4.21 3.99 | 1.90(s,3H), 2.20-2.43(m,3H), 2.60-2.97 (m,2H), 3.23-3.45(m,3H), 3.73-4.40(m,2H), 6.73(s,1H), 7.40(s,1H) |
| 20 | CH₂C(=O)CH₃ | mp (°C.) 177.5-178.0 | 53.95 4.24 3.93 | 53.88 4.18 3.89 | 1.92(s,3H), 2.30(s,3H), 2.20-2.47(m,3H), 3.26-3.50(m,2H), 4.45(s,2H), 6.58(s,3H), 7.48(s,1H) |
| 21 | (cis) CH₂CH=CHCl | Viscous liquid | 51.29 3.76 3.73 | 51.19 3.71 3.75 | 1.93(s,3H), 2.26-2.43(m,3H), 3.26-3.48 (m,2H), 4.77(d,2H), 5.77-6.33(m,2H), 6.70(s,1H), 7.47(s,1H) |
| 22 | (trans) CH₂CH=CHCl | mp (°C.) 145.0-145.5 | 51.29 3.76 3.73 | 51.28 3.79 3.82 | 1.93(s,3H), 2.26-2.43(m,3H), 3.23-3.46 (m,2H), 4.47(d,2H), 5.73-6.50(m,2H), 6.65(s,1H), 7.43(s,1H) |
| 23 | (cis) CH₂CH=C(CH₃)(Cl) | mp (°C.) 102.6-103.0 | 52.53 4.14 3.60 | 52.47 4.16 3.57 | 1.93(s,3H), 2.13(s,3H), 2.26-2.43(m,3H), 3.25-3.50(m,2H), 4.26(d,2H), 5.87(m,1H), 6.65(s,1H), 7.43(s,1H) |
| 24 | (trans) CH₂CH=C(Cl)(CH₃) | mp (°C.) 149.5-150.3 | 52.53 4.14 3.60 | 52.46 4.12 3.66 | 1.90(s,3H), 2.00-2.20(m,3H), 2.23-2.40 (m,3H), 3.26-3.47(m,2H), 4.60(d,2H), 5.67(m,1H), 6.68(s,1H), 7.41(s,1H) |
| 25 | CH₂–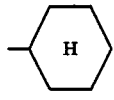 | mp (°C.) 107.8-108.8 | 61.55 4.39 3.58 | 61.44 4.28 3.55 | 1.87(s,3H), 2.18-2.43(m,3H), 3.17-3.43 (m,2H), 4.93(s,2H), 6.70(s,1H), 7.20(s,5H), 7.37(s,1H) |

TABLE 1A-continued

| Compound No. | R[1] | Physical property | Elemental analysis (%) Calculated value C | H | N | Found value C | H | N | $^1$H-NMR Spectral Data (δ: CDCl3) |
|---|---|---|---|---|---|---|---|---|---|
| 26 | CH2—C6H4—Cl | mp (°C.) 88.1–88.9 | 56.56 | 3.79 | 3.29 | 56.51 | 3.77 | 3.25 | 1.87(s,3H), 2.20–2.43(m,3H), 3.26–3.46 (m,2H), 4.93(s,2H), 6.72(s,1H), 7.23(s,4H), 7.40(s,1H) |
| 27 | CH3\|CH—C6H5 | Viscous liquid | 62.38 | 4.73 | 3.46 | 62.35 | 4.69 | 3.34 | 1.63(d,3H), 1.88(s,3H), 2.25–2.45(m,3H), 3.25–3.45(m,2H), 5.23(q,1H), 6.56(s,1H), 7.23(s,5H), 7.40(s,1H) |
| 28 | CH2CH2—C6H5 | Viscous liquid | 62.38 | 4.73 | 3.46 | 62.31 | 4.66 | 3.41 | 1.87(s,3H), 2.20–2.38(m,3H), 3.03(t,2H), 3.20–3.43(m,2H), 4.10(t,2H), 6.60(s,1H), 7.15(s,5H), 7.37(s,1H) |
| 29 | CH2CN | mp (°C.) 153.1–153.8 | 53.11 | 3.56 | 8.25 | 53.08 | 3.51 | 8.18 | 1.92(s,3H), 2.20–2.45(m,3H), 3.25–3.50 (m,2H), 4.73(s,2H), 6.87(s,1H), 7.53(s,1H) |
| 30 | CH3\|CHCN | mp (°C.) 144.5–144.9 | 54.40 | 3.99 | 7.93 | 54.36 | 3.89 | 7.89 | 1.78(d,3H), 1.92(s,3H), 2.20–2.45(m,3H), 3.20–3.43(m,2H), 4.77(q,1H), 6.93(s,1H), 7.47(s,1H) |
| 31 | CH2CH2OC2H5 | Viscous liquid | 54.85 | 5.14 | 3.76 | 54.78 | 5.11 | 3.70 | 1.17(t,3H), 1.90(s,3H), 2.27–2.46(m,3H), 3.26–4.25(m,8H), 6.68(s,1H), 7.35(s,1H) |
| 32 | CH2CH2SCH3 | mp (°C.) 116.5–116.8 | 51.34 | 4.57 | 3.74 | 51.51 | 4.63 | 3.65 | 1.92(s,3H), 2.17(s,3H), 2.25–2.45(s,3H), 2.83(t,3H), 3.25–3.43(m,2H), 4.10(t,3H), 6.60(s,1H), 7.40(s,1H) |
| 33 | CH2COOCH3 | mp (°C.) 106.0–106.5 | 51.63 | 4.06 | 3.76 | 51.49 | 4.08 | 3.85 | 1.90(s,3H), 2.23–2.40(m,3H), 3.25–3.44 (m,2H), 3.70(s,3H), 4.57(s,2H), 6.60 (s,1H), 7.38(s,1H) |
| 34 | CH3\|CHCOOCH3 | mp (°C.) 137.2–138.5 | 52.86 | 4.43 | 3.62 | 52.79 | 4.56 | 3.81 | 1.62(d,3H), 1.90(s,3H), 2.25–2.40(m,3H), 3.25–3.43(m,2H), 3.68(s,3H), 4.68(q,1H), 6.63(s,1H), 7.40(s,1H) |
| 35 | CH3\|CHCOOC2H5 | mp (°C.) 127.5–128.3 | 54.00 | 4.75 | 3.50 | 54.10 | 4.73 | 3.48 | 1.20(t,3H) 1.60(d,3H), 1.93(s,3H), 2.23–2.40(m,3H), 3.26–3.46(m,2H), 4.13 (q,2H), 4.63(q,1H), 6.67(s,H), 7.45(s,1H) |
| 36 | CH3\|CCOOC2H5\|CH3 | mp (°C.) 140.7–141.2 | 55.08 | 5.10 | 3.38 | 55.17 | 5.11 | 3.32 | 1.26(t,3H), 1.60(s,6H), 1.90(s,3H), 2.23–2.43(m,3H), 3.23–3.45(m,2H), 4.15(q,2H), 6.70(s,1H), 7.43(s,1H) |
| 37 | C2H5\|CHCOOC2H5 | Viscous liquid | 55.08 | 5.10 | 3.38 | 55.06 | 5.17 | 3.35 | 1.08(t,3H), 1.20(t,3H), 1.90(s,3H), 1.93 (m,2H), 2.20–2.43(m,3H), 3.25–3.43(m,2H), 4.15(q,2H), 4.46(t,1H), 6.60(s,1H), 7.43(s,1H) |
| 38 | CH2CH=CHCOOCH3 | mp (°C.) 157.3–157.7 | 54.28 | 4.30 | 3.51 | 54.26 | 4.21 | 3.50 | 1.92(s,3H), 2.26–2.50(m,3H), 3.21–3.50 (m,2H), 3.70(s,3H), 4.55–4.80(m,2H), 5.93–7.20(m,3H), 7.43(s,1H) |
| 39 | CH2CF3 | mp (°C.) 102.0–102.5 | 47.14 | 3.16 | 3.66 | 47.10 | 3.09 | 3.69 | 1.93(s,3H), 2.23–2.42(m,3H), 3.25–3.45 (m,2H), 4.32(q,2H), 6.75(s,1H), 7.50(s,1H) |
| 40 | CH2CH(OC2H5)2 | Viscous liquid | 54.81 | 5.56 | 3.36 | 54.87 | 5.48 | 3.33 | 1.20(t,6H), 1.92(s,3H), 2.23–2.45(m,3H), 3.20–4.23(m,7H), 4.50–4.90(m,2H), 6.70(s,1H), 7.40(s,1H) |
| 41 | cyclopentanone-2-yl | Viscous liquid | 56.54 | 4.45 | 3.67 | 56.51 | 4.42 | 3.69 | 1.00–2.80(m,12H), 3.21–3.46(m,2H), 4.46(t,1H), 6.93(s,1H), 0.43(s,1H) |

TABLE 1A-continued

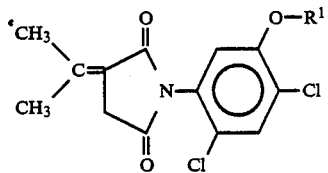

| Compound No. | R¹ | Physical property | Calculated value C | H | N | Found value C | H | N | ¹H-NMR Spectral Data (δ: CDCl₃) |
|---|---|---|---|---|---|---|---|---|---|
| 42 | CH₂CH=CH—C₆H₅ | Viscous liquid | 63.46 | 4.57 | 3.37 | 63.39 | 4.62 | 3.33 | 1.92(s,3H), 2.26–2.47(m,3H), 3.26–2.50 (m,2H), 4.66(d,2H), 6.03–7.63(m,9H) |
| 43 | CH₂C(=O)C₆H₅ | mp (°C.) 175.0–175.2 | 60.29 | 4.07 | 3.35 | 60.27 | 4.02 | 3.30 | 1.90(s,3H), 2.22–2.40(m,3H), 3.25–3.40 (m,2H), 5.23(s,2H), 6.70(s,1H), 7.20–8.06(m,6H) |
| 44 | CH₂C(Cl)=CH₂ | Viscous liquid | 51.29 | 3.76 | 3.73 | 51.22 | 3.78 | 3.75 | 1.90(s,3H), 2.23–2.43(m,3H), 3.25–3.45 (m,2H), 4.43–4.60(m,2H), 5.27–5.63(m,2H), 6.65(s,1H), 7.43(s,1H) | s: singlet,
d: doublet,
t: triplet,
q: quartet,
m: multiplet,
b: broad

TABLE 1B

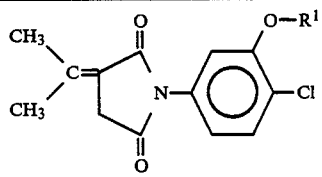

| Compound No. | R¹ | Physical property | Calculated value C | H | N | Found value C | H | N | ¹H-NMR Spectral Data (δ: CDCl₃) |
|---|---|---|---|---|---|---|---|---|---|
| 45 | CH₃ | mp (°C.) 139.4–140.1 | 60.11 | 5.04 | 5.00 | 60.23 | 5.21 | 5.18 | 1.93(s,3H), 2.30–2.50(m,3H), 3.30–3.53 (m,2H), 3.88(s,3H), 6.73–7.58(m,3H) |
| 46 | C₂H₅ | mp (°C.) 118.8–119.7 | 61.33 | 5.48 | 4.76 | 61.11 | 5.62 | 4.57 | 1.41(t,3H), 1.90(s,3H), 2.33–2.47(m,3H), 3.16–3.43(m,2H), 4.03(q,2H), 6.56–7.47(m,3H) |
| 47 | n-C₄H₉ | mp (°C.) 76.5–77.2 | 63.45 | 6.26 | 4.35 | 63.34 | 6.38 | 4.13 | 0.77–2.07(m,10H), 2.27–2.50(m,3H), 3.20–3.43(m,2H), 3.93(t,2H), 6.60–7.50(m,3H) |
| 48 | i-C₃H₇ | mp (°C.) 76.9–77.5 | 62.44 | 5.89 | 4.55 | 62.15 | 5.78 | 4.52 | 1.37(d,6H), 1.89(s,3H), 2.27–2.50(m,3H), 3.20–3.50(m,2H), 4.23–4.87(m,1H), 6.73–7.57(m,3H) |
| 49 | H | mp (°C.) 164.8–165.7 | 58.76 | 4.55 | 5.27 | 58.93 | 4.33 | 5.50 | 1.93(s,3H), 2.30–2.50(m,3H), 3.20–3.40(m,2H), 6.50–7.27(m,3H), 10.03(s,1H) |
| 50 | CH₂CH=CH₂ | mp (°C.) 109.8–110.3 | 62.85 | 5.27 | 4.58 | 62.81 | 5.02 | 4.73 | 1.90(s,3H), 2.23–2.43(m,3H), 3.18–3.43 (m,2H), 4.30–4.67(m,2H), 5.00–6.33(m,3H), 6.65–7.46(m,3H) |
| 51 | CH₂C≡CH | mp (°C.) 161.5–162.2 | 63.26 | 4.64 | 4.61 | 63.61 | 4.48 | 4.68 | 1.90(s,3H), 2.20–2.56(m,4H), 3.20–3.43 (m,2H), 4.65(d,2H), 6.67–7.50(m,3H) |
| 52 | CH₃CHCH=CH₂ | Viscous liquid | 63.85 | 5.67 | 4.38 | 63.53 | 5.89 | 4.48 | 1.50(d,3H), 1.97(s,3H), 2.30–2.53(m,3H), 3.27–3.50(m,2H), 4.30–6.10(m,4H), 6.67–7.50(m,3H) |
| 53 | CH₂CH₂Cl | mp (°C.) 131.7–132.1 | 54.89 | 4.60 | 4.26 | 54.48 | 4.38 | 4.17 | 1.90(s,3H), 2.30–2.47(m,3H), 3.22–3.36 (m,2H), 3.63–4.30(m,4H), 6.63–7.47(m,3H) |
| 54 | CH₂CH₂OH | mp (°C.) 132.0–132.2 | 58.16 | 5.20 | 4.52 | 58.03 | 5.51 | 4.29 | 1.90(s,3H), 2.22–2.63(m,3H), 3.22–3.46 (m,2H), 3.80–4.50(m,5H), 6.88–7.70(m,3H) |
| 55 | CH₂CH(–O–)CH₂ (epoxide) | mp (°C.) 128.6–128.8 | 59.72 | 5.01 | 4.53 | 59.48 | 5.11 | 4.45 | 1.90(s,3H), 2.23–2.47(m,3H), 2.60–2.97 (m,2H), 3.22–3.50(m,2H), 3.80–4.30(m,3H), 6.68–7.46(m,3H) |

TABLE 1B-continued

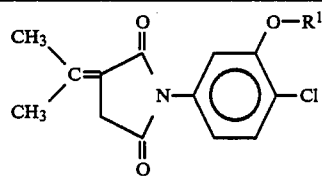

| Compound No. | R[1] | Physical property | Elemental analysis (%) Calculated value C H N | Found value C H N | $^1$H-NMR Spectral Data (δ: CDCl₃) |
|---|---|---|---|---|---|
| 56 | O‖CH₂CCH₃ | mp (°C.) 173.8–174.4 | 59.72 5.01 4.53 | 59.35 5.18 4.33 | 1.83–2.00(m,3H), 2.23–2.46(m,6H), 3.20–3.46(m,2H), 4.43(s,2H), 6.70–7.53(m,3H) |
| 57 | CH₂OCH₃ | mp (°C.) 139.2–139.8 | 58.16 5.20 4.52 | 58.02 5.30 4.45 | 1.83–2.00(m,3H), 2.26–2.46(m,3H), 3.20–3.40(m,2H), 3.41(s,3H), 5.17(s,2H), 6.66–7.47(m,3H) |
| 58 | CH₂CH₂OC₂H₅ | mp (°C.) 102.5–102.8 | 60.44 5.96 4.14 | 60.27 5.91 4.05 | 1.20(t,3H), 1.92(s,3H), 2.23–2.46(m,3H), 3.20–4.33(m,8H), 6.66–7.46(m,3H) |
| 59 | CH₂S·CH₃ | mp (°C.) 138.0–138.2 | 55.29 4.94 4.26 | 54.98 4.82 4.30 | 1.92(s,3H), 2.13–2.46(m,6H), 3.20–3.46(m,2H), 5.13(s,2H), 6.70–7.50(m,3H) |
| 60 | cyclohexyl | mp (°C.) 103.5–103.9 | 65.60 6.37 4.02 | 65.93 6.31 4.19 | 1.03–2.53(m,16H), 3.23–3.46(m,2H), 3.90–4.56(m,1H), 6.60–7.50(m,3H) |
| 61 | CH₂–phenyl | mp (°C.) 102.1–103.0 | 67.51 5.09 3.93 | 67.31 5.17 3.87 | 1.88(s,3H), 2.26–2.43(m,3H), 3.18–3.46(m,2H), 5.03(s,2H), 6.60–7.50(m,8H) |
| 62 | CH₃\|CHCN | mp (°C.) 130.7–130.9 | 60.28 4.74 8.78 | 60.39 4.70 8.75 | 1.78(d,3H), 1.93(s,3H), 2.28–2.50(m,3H), 3.25–3.47(m,3H), 4.85(q,1H), 6.80–7.50(m,3H) |
| 63 | CH₃\|CHCOOCH₃ | Viscous liquid | 58.04 5.15 3.98 | 58.21 5.09 3.80 | 1.63(d,3H), 1.90(s,3H), 2.27–2.45(m,3H), 3.20–3.43(m,2H), 3.70(s,3H), 4.70(q,1H), 6.70–7.48(m,3H) |
| 64 | CH₃\|CHCOOC₂H₅ | Viscous liquid | 59.10 5.51 3.82 | 59.20 5.39 3.88 | 1.20(t,3H), 1.65(d,3H), 1.90(s,3H), 2.27–2.50(m,3H), 3.26–3.50(m,2H), 4.17(q,2H), 4.70(q,1H), 6.77–7.50(m,3H) |

TABLE 1C

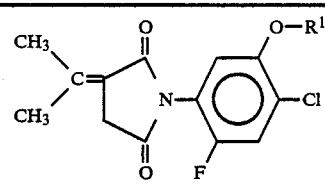

| Compound No. | R[1] | Physical property | Elemental analysis (%) Calculated value C H N | Found value C H N | $^1$H-NMR Spectral Data (δ: CDCl₃) |
|---|---|---|---|---|---|
| 65 | C₂H₅ | mp (°C.) 106.1–106.5 | 57.79 4.84 4.49 | 57.53 4.68 4.56 | 1.40(t,3H), 1.90(s,3H), 2.23–2.46(m,3H), 3.26–3.50(m,2H), 4.00(q,2H), 6.57–7.30(m,2H) |
| 66 | n-C₄H₉ | Viscous liquid | 60.09 5.63 4.12 | 60.18 5.51 4.29 | 0.77–2.03(m,10H), 2.27–2.46(m,3H), 3.23–3.47(m,2H), 3.90(t,2H), 6.56–7.30 (m,2H) |
| 67 | i-C₃H₇ | Viscous liquid | 58.99 5.25 4.29 | 58.72 5.37 4.11 | 1.30(d,6H), 1.87(s,3H), 3.20–3.46(m,3H), 3.22–3.47(m,2H), 4.37(m,1H), 6.60–7.30(m,2H) |
| 68 | cyclohexyl | Viscous liquid | 62.38 5.78 3.82 | 62.15 5.73 3.90 | 1.05–2.55(m,16H), 3.20–3.46(m,2H), 3.90–4.50(m,1H), 6.57–7.27(m,2H) |
| 69 | H | Viscous | 55.04 3.90 4.93 | 55.13 3.97 4.69 | 1.90(s,3H), 2.27–2.46(m,3H), 3.20–3.50 |

TABLE 1C-continued

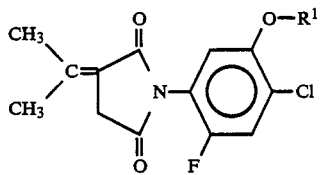

| Compound No. | $R^1$ | Physical property | Elemental analysis (%) Calculated value C | H | N | Found value C | H | N | $^1$H-NMR Spectral Data (δ: CDCl$_3$) |
|---|---|---|---|---|---|---|---|---|---|
| | | liquid | | | | | | | (m,2H), 6.20(b,1H), 6.60–7.30(m,2H) |
| 70 | CH$_2$CH=CH$_2$ | mp (°C.) 77.8–78.7 | 59.35 | 4.66 | 4.32 | 59.14 | 4.77 | 4.29 | 1.93(s,3H), 2.27–2.48(m,3H), 3.25–3.46 (m,2H), 4.30–4.65(m,2H), 5.10–6.30(m,3H), 6.65–7.28(m,2H) |
| 71 | CH$_2$C≡CH | mp (°C.) 134.7–135.5 | 59.73 | 4.07 | 4.53 | 59.55 | 4.16 | 4.51 | 1.92(s,3H), 2.25–2.60(m,4H), 3.28–3.50 (m,2H), 4.66(d,2H), 6.80–7.35(m,2H) |
| 72 | CH$_2$CH$_2$Cl | mp (°C.) 94.1–94.6 | 52.04 | 4.07 | 4.04 | 52.28 | 4.00 | 4.19 | 1.90(s,3H), 2.25–2.46(m,3H), 3.25–3.50 (m,2H), 3.60–4.33(m,4H), 6.63–7.30(m,2H) |
| 73 | CH$_2$CH$_2$OH | mp (°C.) 92.2–92.8 | 54.97 | 4.61 | 4.27 | 54.82 | 4.39 | 4.33 | 1.90(s,3H), 2.20–2.40(m,3H), 3.28–3.46 (m,2H), 3.65–4.23(m,5H), 6.70–7.30(m,2H) |
| 74 | CH$_2$CH—CH$_2$ (epoxide) | mp (°C.) 52.9–53.8 | 56.56 | 4.44 | 4.12 | 56.28 | 4.18 | 4.08 | 1.90(s,3H), 2.26–2.45(m,3H), 2.60–2.97 (m,2H), 3.15–3.60(m,3H), 3.75–4.40(m,2H), 6.70–7.30(m,2H) |
| 75 | CH$_2$CCH$_3$ (O) | mp (°C.) 166.2–166.4 | 56.56 | 4.44 | 4.12 | 56.77 | 4.23 | 4.46 | 1.92(s,3H), 2.20–2.45(m,6H), 3.25–3.50 (m,2H), 4.43(s,2H), 6.57–7.30(m,2H) |
| 76 | CH$_2$OCH$_3$ | Viscous liquid | 54.97 | 4.61 | 4.27 | 54.78 | 4.38 | 4.18 | 1.90(s,3H), 2.20–2.43(m,3H), 3.20–3.55 (m,5H), 5.10(s,2H), 6.90–7.30(m,2H) |
| 77 | CH$_2$CH$_2$OC$_2$H$_5$ | Viscous liquid | 57.38 | 5.38 | 3.93 | 57.30 | 5.29 | 3.86 | 1.17(t,3H), 1.90(s,3H), 2.20–2.40(m,3H), 3.20–4.23(m,8H), 6.60–7.27(m,2H) |
| 78 | CH$_2$–C$_6$H$_5$ | mp (°C.) 104.2–105.0 | 64.26 | 4.58 | 3.74 | 64.12 | 4.51 | 3.66 | 1.93(s,3H), 2.25–2.40(m,3H), 3.26–3.50 (m,2H), 5.02(s,2H), 6.70–7.50(m,7H) |
| 79 | CH$_2$CN | mp (°C.) 138.9–139.7 | 55.82 | 3.74 | 5.88 | 55.63 | 3.54 | 5.94 | 1.90(s,3H), 2.20–2.50(m,3H), 3.23–3.50 (m,2H), 4.75(s,2H), 6.83–7.34(m,2H) |
| 80 | CH$_3$\|CHCN | Viscous liquid | 57.06 | 4.19 | 8.31 | 57.30 | 4.27 | 8.15 | 1.66–2.10(m,6H), 2.26–2.50(m,3H), 3.26–3.50(m,2H), 4.73(q,1H), 6.87–7.30 (m,2H) |
| 81 | CH$_2$COOC$_2$H$_5$ | mp (°C.) 43.5–44.2 | 55.21 | 4.63 | 3.78 | 55.01 | 4.48 | 3.86 | 1.26(t,3H), 1.90(s,3H), 2.20–2.50(m,3H), 3.17–3.46(m,2H), 4.17(q,2H), 4.57(s,2H), 6.60–7.30(m,2H) |
| 82 | CH$_3$\|CHCOOCH$_3$ | Viscous liquid | 55.21 | 4.63 | 3.78 | 55.42 | 4.84 | 3.91 | 1.60(d,3H), 1.90(s,3H), 2.22–2.46(m,3H), 3.20–3.50(m,2H), 3.67(s,3H), 4.60(q,1H), 6.60–7.30(m,2H) |
| 83 | CH$_3$\|CHCOOC$_2$H$_5$ | Viscous liquid | 56.33 | 4.98 | 3.64 | 56.52 | 4.91 | 3.77 | 1.21(t,3H), 1.60(d,3H), 1.90(s,3H), 2.26–2.40(m,3H), 3.26–3.43(m,2H), 4.13(q,2H), 4.58(q,1H), 6.60–7.28(m,3H) |
| 84 | CH$_3$\|CHCH=CH$_2$ | Viscous liquid | 60.44 | 5.04 | 4.15 | 60.21 | 5.18 | 4.11 | 1.43(d,3H), 1.88(s,3H), 2.28–2.40(m,3H), 3.19–3.46(m,2H), 4.30–6.26(m,4H), 6.60–7.26(m,2H) |

TABLE 1D

[Structure: succinimide with isopropylidene substituent attached to N-phenyl ring bearing Cl and X substituents, and NHCH(R²)C(O)N(R³)(R⁴) group]

| Compound No. | R² | R³ | R⁴ | X | Physical property | TLC Rf value | ¹H-NMR Spectral Data (δ: CDCl₃) |
|---|---|---|---|---|---|---|---|
| 85 | CH₃ | n-C₃H₇ | H | H | Viscous liquid | 0.52 | 0.63–1.66(m,8H), 1.90(s,3H), 2.33(m,3H), 3.00–3.90(m,5H), 4.56(b,1H), 6.30–7.40(m,4H) |
| 86 | CH₃ | n-C₄H₉ | H | H | Viscous liquid | 0.56 | 0.66–1.80(m,10H), 1.90(s,3H), 2.30(m,3H), 2.95–4.00(m,5H), 4.50(b,1H), 6.33–7.40(m,4H) |
| 87 | CH₃ | sec-C₄H₉ | H | H | mp (°C.) 58.5–59.5 | 0.43 | 0.66–1.66(m,11H), 1.93(s,3H), 2.30(m,3H), 3.30(m,2H), 3.70(m,1H), 4.53(b,1H), 6.10–7.40(m,4H) |
| 88 | CH₃ | iso-C₅H₁₁ | H | H | Viscous liquid | 0.60 | 0.73–1.66(m,12H), 1.87(s,3H), 2.30(m,3H), 3.00–4.00(m,5H), 4.60(b,1H), 6.33–7.40(m,4H) |
| 89 | CH₃ | CH₂CH=CH₂ | H | H | Viscous liquid | 0.52 | 1.56(d,3H), 1.93(s,3H), 2.33(m,3H), 3.30(m,2H), 3.60–4.20(m,3H), 4.30–6.00(m,3H), 6.33–7.40(m,4H) |
| 90 | CH₃ | CH₂C≡CH | H | H | Viscous liquid | 0.52 | 1.53(d,3H), 1.90(s,3H), 2.10(m,1H), 2.30(m,3H), 3.30(m,2H), 3.60–4.10(m,3H), 4.65(b,1H), 6.30–7.40(m,4H) |
| 91 | CH₃ | C(CH₃)₂C≡CH | H | H | Viscous liquid | 0.58 | 1.23–1.75(m,9H), 1.90(s,3H), 2.23–2.50(m,4H), 3.35(m,2H), 3.66(m,1H), 4.63(b,1H), 6.35–7.40(m,4H) |
| 92 | CH₃ | cyclopropyl | H | H | Viscous liquid | 0.45 | 0.23–0.80(m,4H), 1.50(d,3H), 1.87(s,3H), 2.30(m,3H), 2.63(m,1H), 3.26(m,2H), 3.68(m,1H), 4.63(b,1H), 6.26–7.35(m,4H) |
| 93 | CH₃ | cyclopentyl | H | H | Viscous liquid | 0.56 | 1.00–2.00(m,14H), 2.33(m,3H), 3.30(m,2H), 3.50–4.35(m,2H), 4.66(b,1H), 6.33–7.40(m,4H) |
| 94 | CH₃ | cyclohexyl | H | H | Viscous liquid | 0.61 | 0.83–1.95(m,16H), 2.30(m,3H), 3.20–3.90(m,4H), 4.60(b,1H), 6.30–7.37(m,4H) |
| 95 | H | cyclohexyl | H | H | Viscous liquid | 0.52 | 0.75–2.10(m,13H), 2.30(s,3H), 3.15–4.00(m,5H), 5.20(b,1H), 6.33–7.35(m,4H) |
| 96 | H | sec-C₄H₉ | H | H | Viscous liquid | 0.49 | 0.60–1.60(m,11H), 1.87(s,3H), 2.30(m,3H), 3.25(m,2H), 3.50–4.10(m,3H), 5.20(b,1H), 6.33–7.33(m,4H) |
| 97 | CH₃ | CH₂-phenyl | H | H | Viscous liquid | 0.60 | 1.55(d,3H), 1.90(s,3H), 2.33(m,3H), 3.28(m,2H), 3.60–4.50(m,3H), 4.60(b,1H), 6.35–7.35(m,9H) |
| 98 | CH₃ | CH₂CH₂OCH₃ | H | H | Viscous liquid | 0.38 | 1.50(d,3H), 1.90(s,3H), 2.33(s,3H), 3.18–3.50(m,9H), 3.90(m,1H), 4.66(b,1H), 6.33–7.40(m,4H) |
| 99 | CH₃ | CH₂COOC₂H₅ | H | H | Viscous liquid | 0.49 | 1.20(t,3H), 1.53(d,3H), 1.90(s,3H), 2.30(s,3H), 3.27(m,2H), 3.50–4.33(m,5H), 4.80(b,1H), 6.33–7.40(m,4H) |
| 100 | CH₃ | n-C₃H₇ | H | Cl | Viscous liquid | 0.52 | 0.60–1.80(m,8H), 1.93(s,3H), 2.33(s,3H), 2.97–3.97(m,5H), 4.60(b,1H), 6.26(s,1H), 6.53(b,1H), 7.36(s,1H) |
| 101 | CH₃ | iso-C₃H₇ | H | Cl | Viscous liquid | 0.52 | 0.97–1.30(m,6H), 1.50(d,3H), 1.90(s,3H), 2.33(m,3H), 3.33(m,2H), 3.45–4.40(m,2H), 4.60(b,1H), 6.30(m,2H), 7.37(s,1H) |
| 102 | CH₃ | sec-C₄H₉ | H | Cl | Viscous liquid | 0.41 | 0.63–1.66(m,11H), 1.90(s,3H), 2.30(s,3H), 3.33(m,2H), 3.43–4.20(m,3H), 4.60(b,1H), 6.17(b,1H), 6.30(s,1H), 7.37(s,1H) |
| 103 | CH₃ | C₂H₅ | C₂H₅ | Cl | Viscous | 0.51 | 0.90–1.50(m,9H), 1.93(s,3H), 2.35(m,3H), |

TABLE 1D-continued

| Compound No. | R² | R³ | R⁴ | X | Physical property | TLC Rf value | ¹H-NMR Spectral Data (δ: CDCl₃) |
|---|---|---|---|---|---|---|---|
| | | | | | liquid | | 3.10–3.60(m,6H), 4.15(m,1H), 5.60(b,1H), 6.33(s,1H), 7.33(s,1H) |
| 104 | CH₃ | OCH₃ | CH₃ | Cl | Viscous liquid | 0.64 | 1.40(d,3H), 1.90(s,3H), 2.33(m,3H), 3.17(s,3H), 3.33(m,2H), 3.67(s,3H), 4.45(m,1H), 5.30(b,1H), 6.40(s,1H), 7.30(s,1H) |
| 105 | CH₃ | CH₃ | H | F | Viscous liquid | 0.38 | 1.53(d,3H), 1.90(s,3H), 2.33(m,3H), 2.77(d,3H), 3.37(m,2H), 3.65(m,1H), 4.45(b,1H), 6.27–7.35(m,3H) |
| 106 | CH₃ | n-C₃H₇ | H | F | Viscous liquid | 0.50 | 0.66–1.70(m,8H), 1.90(s,3H), 2.30(s,3H), 2.90–3.90(m,5H), 4.40(b,1H), 6.20–7.27(m,3H) |
| 107 | CH₃ | sec-C₄H₉ | H | F | Viscous liquid | 0.56 | 0.70–1.60(m,11H), 1.93(s,3H), 2.33(m,3H), 3.33(m,2H), 3.50–4.10(m,2H), 4.40(b,1H), 6.17–7.30(m,3H) |
| 108 | CH₃ | iso-C₅H₁₁ | H | F | Viscous liquid | 0.59 | 0.73–1.66(m,11H), 1.90(s,3H), 2.33(m,3H), 3.30(m,2H), 3.60(m,1H), 4.33(b,1H), 6.20–7.30(m,3H) |
| 109 | CH₃ | CH₂CH=CH₂ | H | F | Viscous liquid | 0.51 | 1.53(d,3H), 1.93(s,3H), 2.33(m,3H), 3.33(m,2H), 3.80(m,2H), 4.40(b,1H), 4.80–6.10(m,3H), 6.20–7.27(m,3H) |
| 110 | CH₃ | CH₂C≡CH | H | F | Viscous liquid | 0.50 | 1.50(d,3H), 1.90(s,3H), 2.25(m,1H), 2.30(m,3H), 3.33(m,2H), 3.50–4.10(m,3H), 4.43(b,1H), 6.20–7.30(m,3H) |
| 111 | CH₃ |  | H | F | Viscous liquid | 0.44 | 0.30–0.90(m,4H), 1.47(d,3H), 1.90(s,3H), 2.30(m,3H), 2.67(m,1H), 3.33(m,2H), 3.66(m,1H), 4.37(b,1H), 6.27–7.30(m,3H) |
| 112 | CH₃ |  | H | F | Viscous liquid | 0.57 | 0.80–2.05(m,16H), 2.30(m,3H), 3.30(m,2H), 3.60(m,2H), 4.35(b,1H), 6.20–7.30(m,3H) |
| 113 | CH₃ | 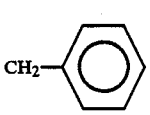 | H | H | Viscous liquid | 0.62 | 1.66(d,3H), 1.87(s,3H), 2.30(m,3H), 3.30(m,2H), 4.63(b,1H), 6.47–7.60(m,8H), 8.33(b,1H) |
| 114 | CH₃ | CH₂CH₂OCH₃ | H | F | Viscous liquid | 0.38 | 1.50(d,3H), 1.93(s,3H), 2.30(m,3H), 3.10–4.00(m,10H), 4.45(b,1H), 6.20–7.30(m,3H) |
| 115 | CH₃ | CH₂CH₂OH | H | F | Viscous liquid | 0.15 | 1.55(d,3H), 1.90(s,3H), 2.30(s,3H), 2.60–4.00(m,7H), 4.50(b,1H), 6.17–7.35(m,3H) |
| 116 | CH₃ |  | H | F | Viscous liquid | 0.55 | 1.53(d,3H), 1.90(s,3H), 2.30(m,3H), 3.30(2H), 3.67(m,1H), 4.35(m,2H), 6.30–7.33(m,8H) |
| 117 | CH₃ | CH₂COOC₂H₅ | H | F | Viscous liquid | 0.49 | 1.23(t,3H), 1.55(d,3H), 1.90(s,3H), 2.33(m,3H), 3.33(m,2H), 3.47–4.35(m,5H), 4.47(b,1H), 6.30–7.33(m,3H) |
| 118 | CH₃ |  | H | Cl | Viscous liquid | 0.49 | 1.35(d,3H), 1.93(s,3H), 2.35(m,3H), 3.20–3.85(m,10H), 4.20(m,1H), 5.55(b,1H), 6.33(s,1H), 7.35(s,1H) |
| 119 | CH₃ | | H | Cl | Viscous liquid | 0.69 | 1.20–1.80(m,9H), 1.87(s,3H), 2.30(m,3H), 3.10–3.70(m,6H), 4.30(m,1H), 5.66(b,1H), 6.30(s,1H), 7.30(s,1H) |
| 120 | CH₃ | CH₂CH=CH₂ | CH₂CH=CH₂ | Cl | Viscous liquid | 0.69 | 1.36(d,3H), 1.90(s,3H), 2.33(m,3H), 3.35(m,2H), 3.50–6.10(m,12H), 6.33(s,1H), 7.33(s,1H) |

TABLE 1D-continued $$\text{Structure with } R^2, R^3, R^4, \text{CH}_3, \text{Cl, X substituents on pyrrolidinedione-phenyl-amide scaffold}$$

| Compound No. | $R^2$ | $R^3$ | $R^4$ | X | Physical property | TLC Rf value | $^1$H-NMR Spectral Data ($\delta$: CDCl$_3$) |
|---|---|---|---|---|---|---|---|
| 121 | CH$_3$ | CH$_2$CH$_2$CN | H | H | Viscous liquid | 0.35 | 1.56(d,3H), 1.95(s,3H), 2.33(m,3H), 2.57(m,2H), 3.20–3.95(m,5H), 4.57(b,1H), 6.33–7.45(m,3H) |
| 122 | CH$_3$ | C$_2$H$_5$ | C$_2$H$_5$ | F | Viscous liquid | 0.48 | 0.93–1.60(m,9H), 1.92(s,3H), 2.35(m,3H), 3.10–3.63(m,6H), 4.22(m,1H), 5.33(b,1H), 6.30–7.30(m,2H) |
| 123 | CH$_3$ | CH$_2$CH=CH$_2$ | CH$_2$CH=CH$_2$ | F | Viscous liquid | 0.60 | 1.40(d,3H), 1.93(s,3H), 2.35(m,3H), 3.35(m,2H), 3.80–6.15(m,12H), 6.30–7.35(m,2H) |
| 124 | CH$_3$ | OCH$_3$ | CH$_3$ | F | Viscous liquid | 0.48 | 1.40(d,3H), 1.92(s,3H), 2.35(m,3H), 3.25(s,3H), 3.37(m,2H), 3.72(s,3H), 4.45(m,1H), 5.05(b,1H), 6.36–7.30(m,3H) |
| 125 | CH$_3$ | O-n-C$_3$H$_7$ | H | F | Viscous liquid | 0.33 | 0.73–2.10(m,8H), 2.33(s,3H), 3.33(m,2H), 3.60–4.70(m,4H), 6.33–7.35(m,2H), 9.46(b,1H) |
| 126 | CH$_3$ | C$_2$H$_5$ | n-C$_3$H$_7$ | F | Viscous liquid | 0.55 | 0.66–1.83(m,11H), 1.93(s,3H), 2.35(m,3H), 3.06–3.73(m,6H), 4.25(m,1H), 5.45(b,1H), 6.30–7.36(m,2H) |
| 127 | CH$_3$ | morpholino (R$^3$–R$^4$ = –(CH$_2$CH$_2$)$_2$O–) | | F | Viscous liquid | 0.30 | 1.36(d,3H), 1.92(s,3H), 3.26–3.83(m,10H), 4.16(m,1H), 5.26(b,1H), 6.30–7.30(m,1H) |

PREPARATION EXAMPLE

Preparation Example 1 (wettable powder)

25 Parts by weight of the compound of the present invention, 5 parts by weight of Sorpol 5039 (trade name of a product of Toho Chemical Industry Company, Japan) and 70 parts by weight of talc are thoroughly pulverized and mixed to obtain a wettable powder.

Preparation Example 2 (emulsifiable concentrate)

5 Parts by weight of the compound of the present invention, 10 parts by weight of Sorpol 3005 X (a product of Toho Chemical Industry Company, Japan), 45 parts by weight of n-butanol and 40 parts by weight of xylene are thoroughly mixed to obtain an emulsifiable concentrate.

Preparation Example 3 (granule)

1 Part by weight of the compound of the present invention, 45 parts by weight of bentonite, 44 parts by weight of clay, 5 parts by weight of sodium lignosulfonate and 5 parts by weight of sodium dodecylbenzenesulfonate are thoroughly pulverized and mixed. To the mixture is added water, and the resultant product is thoroughly kneaded. The kneaded mixture is then subjected to gradulation, followed by drying, thereby to obtain granules.

Preparation Example 4 (dust)

1 Part by weight of the compound of the present invention and 99 parts by weight of clay are thoroughly pulverized and mixed to obtain a dust.

APPLICATION EXAMPLE

Application Example 1

Pots each having a surface area of 1/5000 a were packed with paddy field soil in a greenhouse. In each pot, rice seedlings of 3 leaf stage were transplanted at a depth of 2 to 3 cm from the surface soil. Seeds of barnyardgrass and monochoria, and seeds of broad-leaved annual weeds, toothcup and false pimpernel, were mixed with dry paddy field soil and incorporated into the surface soil. Further, as a perennial weed, seeds of "Hotarui" (*Scirpus juncoides*) were planted.

Using the compounds listed in Table 2, emulsifiable concentrates having a predetermined concentration were prepared according to the method described in Preparation Example 2. Each of the thus prepared concentrates was dropwise applied by means of a pipette when the barnyardgrass grew up to 1.5 to 2.0 leaf stage. 21 Days after the application, phytotoxicity to rice plants and herbicidal effects on weeds were observed. The results obtained were shown in Table 2. The values indicated in Table 2 are based on the following criterion.

5: Perfect inhibition
4: 80% inhibition
3: 60% inhibition
2: 40% inhibition
1: 20% inhibition
0: No effect

TABLE 2

| Compound No. | Dosage (a.i.g/10a) | Herbicidal Effect | | | | Phytotoxicity to rice plant |
|---|---|---|---|---|---|---|
| | | Barnyardgrass | Monochoria | Broad-leaved weeds | Hotarui (Scirpus juncoides) | |
| 1 | 75 | 5 | 5 | 5 | 5 | 0 |
|  | 30 | 5 | 5 | 5 | 5 | 0 |
| 2 | 75 | 5 | 5 | 5 | 5 | 0 |
|  | 30 | 5 | 5 | 5 | 5 | 0 |
| 6 | 75 | 5 | 5 | 5 | 5 | 0 |
|  | 30 | 5 | 5 | 5 | 5 | 0 |
| 10 | 75 | 5 | 5 | 5 | 5 | 0 |
|  | 30 | 5 | 5 | 5 | 5 | 0 |
| 11 | 75 | 5 | 5 | 5 | 5 | 1 |
|  | 30 | 5 | 5 | 5 | 5 | 0 |
| 25 | 75 | 5 | 5 | 5 | 4 | 0 |
|  | 30 | 4 | 5 | 5 | 3 | 0 |
| 29 | 75 | 5 | 5 | 5 | 5 | 0 |
|  | 30 | 4 | 5 | 5 | 5 | 0 |
| 34 | 75 | 5 | 5 | 5 | 5 | 0 |
|  | 30 | 5 | 5 | 5 | 5 | 0 |
| 45 | 75 | 5 | 5 | 5 | 5 | 0 |
|  | 30 | 5 | 5 | 5 | 5 | 0 |
| 46 | 75 | 5 | 5 | 5 | 5 | 0 |
|  | 30 | 5 | 5 | 5 | 5 | 0 |
| 48 | 75 | 5 | 5 | 5 | 5 | 0 |
|  | 30 | 5 | 5 | 5 | 5 | 0 |
| 50 | 75 | 5 | 5 | 5 | 5 | 0 |
|  | 30 | 5 | 5 | 5 | 5 | 0 |
| 51 | 75 | 5 | 5 | 5 | 5 | 1 |
|  | 30 | 5 | 5 | 5 | 5 | 0 |
| 61 | 75 | 5 | 5 | 5 | 4 | 0 |
|  | 30 | 4 | 5 | 5 | 2 | 0 |
| 62 | 75 | 5 | 5 | 5 | 5 | 0 |
|  | 30 | 4 | 5 | 5 | 4 | 0 |
| 63 | 75 | 5 | 5 | 5 | 5 | 0 |
|  | 30 | 5 | 5 | 5 | 4 | 0 |
| 65 | 30 | 5 | 5 | 5 | 5 | 0 |
|  | 15 | 5 | 5 | 5 | 5 | 0 |
| 66 | 30 | 5 | 5 | 5 | 5 | 0 |
|  | 15 | 5 | 5 | 5 | 5 | 0 |
| 67 | 30 | 5 | 5 | 5 | 5 | 0 |
|  | 15 | 5 | 5 | 5 | 5 | 0 |
| 70 | 30 | 5 | 5 | 5 | 5 | 0 |
|  | 15 | 5 | 5 | 5 | 5 | 0 |
| 71 | 30 | 5 | 5 | 5 | 5 | 1 |
|  | 15 | 5 | 5 | 5 | 5 | 0 |
| 77 | 30 | 5 | 5 | 5 | 4 | 0 |
|  | 15 | 4 | 5 | 5 | 2 | 0 |
| 79 | 30 | 5 | 5 | 5 | 4 | 0 |
|  | 15 | 4 | 5 | 5 | 3 | 0 |
| 82 | 30 | 5 | 5 | 5 | 5 | 0 |
|  | 15 | 4 | 5 | 5 | 4 | 0 |
| 85 | 30 | 5 | 5 | 5 | 5 | 0 |
|  | 15 | 5 | 5 | 5 | 5 | 0 |
| 87 | 30 | 5 | 5 | 5 | 5 | 0 |
|  | 15 | 5 | 5 | 5 | 5 | 0 |
| 89 | 30 | 5 | 5 | 5 | 5 | 0 |
|  | 15 | 5 | 5 | 5 | 4 | 0 |
| 98 | 30 | 5 | 5 | 5 | 5 | 0 |
|  | 15 | 4 | 5 | 4 | 4 | 0 |
| 103 | 30 | 5 | 5 | 5 | 5 | 0 |
|  | 15 | 5 | 5 | 5 | 5 | 0 |
| 106 | 30 | 5 | 5 | 5 | 5 | 1 |
|  | 15 | 5 | 5 | 5 | 5 | 0 |
| 107 | 30 | 5 | 5 | 5 | 5 | 0 |
|  | 15 | 5 | 5 | 5 | 5 | 0 |
| 110 | 30 | 5 | 5 | 5 | 5 | 1 |
|  | 15 | 5 | 5 | 5 | 5 | 0 |
| 111 | 30 | 5 | 5 | 5 | 5 | 0 |
|  | 15 | 5 | 5 | 5 | 5 | 0 |
| 118 | 30 | 5 | 5 | 5 | 5 | 0 |
|  | 15 | 5 | 5 | 5 | 5 | 0 |
| Comparative Compound No. 1 (Note 1) | 75 | 5 | 5 | 5 | 4 | 3 |
|  | 30 | 4 | 4 | 5 | 3 | 2 |
| Comparative Compound No. 2 | 75 | 2 | 3 | 3 | 2 | 0 |

TABLE 2-continued

| Compound No. | Dosage (a.i.g/10a) | Herbicidal Effect | | | | Phytotoxicity to rice plant |
|---|---|---|---|---|---|---|
| | | Barnyardgrass | Monochoria | Broad-leaved weeds | Hotarui (*Scirpus juncoides*) | |
| (Note 2) | | | | | | |

Note 1.
Comparative Compound: No. 1 (Chlorphthalim)

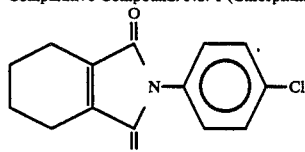

(Used as an emulsifiable concentrate according to Preparation Example 2.)
Note 2.
Comparative Compound: No. 2 (Butachlor)

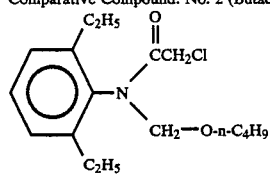

(Used as granules available from NIHON NOYAKU K.K., Japan.)

Application Example 2

Pots each having a surface area of 1/2500 a were packed with upland soil in a greenhouse. In each pot were planted seeds of soybean, Indian corn, crabgrass, livid amaranth and smartweed.

The application was effected, by applying a composition in a dosage of 10 a.i. g/10a, 24 hours after the planting of the seeds. The herbicidal composition was prepared and applied as follows. Using the compounds listed in Table 3, emulsifiable concentrates having a predetermined concentration were prepared according to the method described in Preparation Example 2. Each of the thus prepared concentrates were diluted with 15 g of water per each are of the upland soil, and then applied by means of a glass sprayer. 14 Days after the application, the degree of the herbicidal effect on weeds was observed. 30 Days after the application, the degree of the phytotoxicity to crop plants was observed. The results obtained are shown in Table 3. The criteria for the values indicated in Table 3 are the same as those employed in Application Example 1.

TABLE 3

| Compound No. | Herbicidal Activity and Phytotoxicity | | | | |
|---|---|---|---|---|---|
| | Crabgrass | Livid amaranth | Smart- weed | Soy- bean | Indian corn |
| 1 | 5 | 5 | 4 | 0 | 0 |
| 6 | 5 | 5 | 5 | 0 | 0 |
| 10 | 5 | 5 | 5 | 0 | 0 |
| 11 | 5 | 5 | 5 | 0 | 0 |
| 34 | 5 | 5 | 5 | 0 | 0 |
| 45 | 5 | 5 | 4 | 0 | 0 |
| 46 | 5 | 5 | 5 | 0 | 0 |
| 48 | 5 | 5 | 5 | 0 | 0 |
| 50 | 5 | 5 | 5 | 0 | 0 |
| 51 | 5 | 5 | 5 | 0 | 0 |
| 65 | 5 | 5 | 5 | 0 | 0 |
| 66 | 5 | 5 | 5 | 0 | 0 |
| 67 | 5 | 5 | 5 | 0 | 0 |
| 70 | 5 | 5 | 5 | 0 | 0 |
| 71 | 5 | 5 | 5 | 0 | 0 |
| 87 | 5 | 5 | 5 | 0 | 0 |
| 106 | 5 | 5 | 5 | 0 | 0 |
| 107 | 5 | 5 | 5 | 0 | 0 |
| 110 | 5 | 5 | 5 | 0 | 0 |
| 111 | 5 | 5 | 5 | 0 | 0 |

TABLE 3-continued

| Compound No. | Herbicidal Activity and Phytotoxicity | | | | |
|---|---|---|---|---|---|
| | Crabgrass | Livid amaranth | Smart- weed | Soy- bean | Indian corn |
| 118 | 5 | 5 | 5 | 0 | 0 |
| Comparative Compound No. 1 | 4 | 3 | 3 | 0 | 0 |

What is claimed is:

1. An N-substituted-phenylteraconimide compound represented by the formula

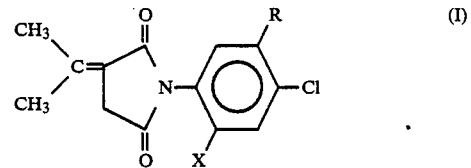

wherein X represents a hydrogen atom, a fluorine atom or a chlorine atom; and

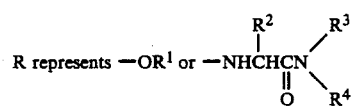

wherein $R^1$ represents a hydrogen atom, a straight chain or branched alkyl group having up to 8 carbon atoms, a straight chain or branched alkenyl group having up to 8 carbon atoms, an alkynyl group having up to 8 carbon atoms, a cycloalkyl group having up to 8 carbon atoms wherein a carbon atom thereof is unsubstituted or substituted with an oxygen atom, a sulfur atom or a carbonyl group, or a straight chain or branched alkyl or alkenyl group having up to 8 carbon atoms and substituted with at least one substituent selected from the group consisting of a halogen atom, a cyano group, a hydroxyl group, an alkoxyl group having up to 8 carbon atoms, an alkylthio group having up to 8 carbon atoms, an epoxy group, a substituted or unsubstituted aromatic hydrocarbon group having up to 8 carbon atoms, an acyl group having up to 8 carbon atoms and an alkoxycarbonyl group having up to 8 carbon atoms, $R^2$ represents a hydrogen atom or a straight chain or branched alkyl group having up to 8 carbon atoms, and $R^3$ and $R^4$ each independently represent a hydrogen atom, a straight chain or branched alkyl group having up to 8 carbon atoms, a straight chain or branched alkenyl group having up to 8 carbon atoms, an alkynyl group having up to 8 carbon atoms, an alkoxyl group having up to 8 carbon atoms, an alkoxyalkyl group having up to 8 carbon atoms, an alkoxycarbonylalkyl group having up to 8 carbon atoms, a cycloalkyl group having up to 8 carbon atoms, a hydroxyalkyl group having up to 8 carbon atoms, a cyanoalkyl group having up to 8 carbon atoms, an aralkyl group having up to 9 carbon atoms or an aryl group having up to 8 carbon atoms, or $R^3$ and $R^4$ are directly bonded with each other, thereby forming with the nitrogen atom bonded therewith a morpholine ring group.

2. A compound according to claim 1, wherein X represents a fluorine atom, and $R^1$ represents a straight chain or branched alkyl group having up to 8 carbon atoms, a straight chain or branched alkenyl group having up to 8 carbon atoms or an alkynyl group having up to 8 carbon atoms.

3. A compound according to claim 1, wherein X represents a chlorine atom, and $R^1$ represents a straight chain or branched alkyl group having up to 8 carbon atoms, a straight chain or branched alkenyl group having up to 8 carbon atoms or an alkynyl group having up to 8 carbon atoms.

4. A compound according to claim 1, wherein x represents a fluorine atom, $R^2$ represents a methyl group, and $R^3$ and $R^4$ are directly bonded with each other, thereby forming with the nitrogen atom bonded therewith a morpholine ring group or $R^3$ represents a straight chain or branched alkyl group having up to 8 carbon atoms, a straight chain or branched alkenyl group having up to 8 carbon atoms, an alkynyl group having up to 8 carbon atoms, an alkoxyl group having up to 8 carbon atoms or a cycloalkyl group having up to 8 carbon atoms, and $R^4$ represents a hydrogen atom, a straight chain or branched alkyl group having up to 8 carbon atoms, a straight chain or branched alkenyl group having up to 8 carbon atoms or an alkynyl group having up to 8 carbon atoms.

5. A compound according to claim 1, wherein x represents a hydrogen atom, $R^2$ represents a methyl group, and $R^3$ and $R^4$ are directly bonded with each other, thereby forming with the nitrogen atom bonded therewith a morpholine ring group, or $R^3$ represents a straight chain or branched alkyl group having up to 8 carbon atoms, a straight chain or branched alkenyl group having up to 8 carbon atoms, an alkynyl group having up to 8 carbon atoms, an alkoxyl group having up to 8 carbon atoms or a cycloalkyl group having up to 8 carbon atoms, and $R^4$ represents a hydrogen atom, a straight chain or branched alkyl group having up to 8 carbon atoms, a straight chain or branched alkenyl group having up to 8 carbon atoms or an alkynyl group having up to 8 carbon atoms.

6. A compound according to claim 1, wherein X represents a fluorine atom, and $R^1$ represents an alkoxyalkyl group having up to 8 carbon atoms.

7. A compound according to claim 1 selected from the group consisting of:
N-(2,4-dichloro-5-propargyloxyphenyl)teraconimide,
N-(2,4-dichloro-5-allyloxyphenyl)teraconimide,
N-(2,4-dichloro-5-isopropoxyphenyl)teraconimide,
N-(2,4-dichloro-5-methoxyphenyl)teraconimide,
N-[2,4-dichloro-5-(1-methylallyloxy)phenyl]-teraconimide,
N-(2-fluoro-4-chloro-5-propargyloxyphenyl)-teraconimide,
N-(2-fluoro-4-chloro-5-allyloxyphenyl)teraconimide,
N-(2-fluoro-4-chloro-5-isopropoxyphenyl)teraconimide,
N-(2-fluoro-4-chloro-5-methoxyphenyl)teraconimide,
N-(2-fluoro-4-chloro-5-methoxymethoxyphenyl)-teraconimide,
N-[2-fluoro-4-chloro-5-(1-methylallyloxy)phenyl]-teraconimide,
N-[5-[1-(N-methoxy-N-methylcarbamoyl)ethylamino]-2-fluoro-4-chlorophenyl]teraconimide,
N-[5-[1-(N,N-diethylcarbamoyl)ethylamino]-2-fluoro-4-chlorophenyl]teraconimide,
N-[5-[1-(N-propoxycarbamoyl)ethylamino]-2-fluoro-4-chlorophenyl]teraconimide, and
N-[5-[1-(N-propargylcarbamoyl)ethylamino]-2-fluoro-4-chlorophenyl]teraconimide.

8. A herbicidal composition which comprises as an active ingredient a herbicidally effective amount of an N-substituted-phenylteraconimide compound represented by the formula

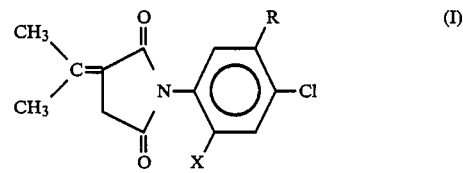

wherein X represents a hydrogen atom, a fluorine atom or a chlorine atom; and

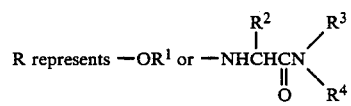

wherein $R^1$ represents a hydrogen atom, a straight chain or branched alkyl group having up to 8 carbon atoms, a straight chain or branched alkenyl group having up to 8 carbon atoms, an alkynyl group having up to 8 carbon atoms, a cycloalkyl group having up to 8 carbon atoms wherein a carbon atom thereof is unsubstituted or substituted with an oxygen atom, a sulfur atom or a carbonyl group, or a straight chain or branched alkyl or alkenyl group having up to 8 carbon atoms and substituted with at least one substituent selected from the group consisting of a halogen atom, a cyano group, a hydroxyl group, an alkoxyl group having up to 8 carbon atoms, an alkylthio group having up to 8 carbon atoms, an epoxy group, a substituted or unsubstituted aromatic hydrocarbon group having up to 8 carbon atoms, an acyl group having up to 8 carbon atoms and an alkoxycarbonyl group having up to 8 carbon atoms, $R^2$ represents a hydrogen atom or a straight chain or branched alkyl group having up to 8 carbon atoms, and $R^3$ and $R^4$ each independently represent a hydrogen atom, a straight chain or branched alkyl group having up to 8 carbon atoms, a straight chain or branched alkenyl group having up to 8 carbon atoms, an alkynyl group having up to 8 carbon atoms, an alkoxyl group having up to 8 carbon atoms, an alkoxyalkyl group having up to 8 carbon atoms, an alkoxycarbonylalkyl group having up to 8 carbon atoms, a cycloalkyl group having up to 8 carbon atoms, a hydroxyalkyl group having up to 8 carbon atoms, a cyanoalkyl group having up to 8 carbon atoms, an aralkyl group having up to 9 carbon atoms or an aryl group having up to 8 carbon atoms, or $R^3$ and $R^4$ are directly bonded with each other, thereby forming with the nitrogen atom bonded therewith a morpholine ring group.

9. A herbicidal composition according to claim 8, wherein X represents a fluorine atom, and $R^1$ represents a straight chain or branched alkyl group having up to 8 carbon atoms, a straight chain or branched alkenyl group having up to 8 carbon atoms or an alkynyl group having up to 8 carbon atoms.

10. A herbicidal composition according to claim 8, wherein X represents a chlorine atom, and $R^1$ represents a straight chain or branched alkyl group having up to 8 carbon atoms, a straight chain or branched alkenyl group having up to 8 carbon atoms or an alkynyl group having up to 8 carbon atoms.

11. A herbicidal composition according to claim 8, wherein X represents a fluorine atom, $R^2$ represents a methyl group, and $R^3$ and $R^4$ are directly bonded with each other, thereby forming with the nitrogen atom bonded therewith a morpholine ring group, or $R^3$ represents a straight chain or branched alkyl group having up to 8 carbon atoms, a straight chain or branched an alkenyl group having up to 8 carbon atoms, an alkynyl group having up to 8 carbon atoms, an alkoxyl group having up to 8 carbon atoms or a cycloalkyl group having up to 8 carbon atoms, and $R^4$ represents a hydrogen atom, a straight chain or branched alkyl group having up to 8 carbon atoms, a straight chain or branched alkenyl group having up to 8 carbon atoms or an alkynyl group having up to 8 carbon atoms.

12. A herbicidal composition according to claim 8, wherein x represents a hydrogen atom, $R^2$ represents a methyl group, and $R^3$ and $R^4$ are directly bonded with each other, thereby forming with the nitrogen atom bonded therewith a morpholine ring group, or $R^3$ represents a straight chain or branched alkyl group having up to 8 carbon atoms, a straight chain or branched alkenyl group having up to 8 carbon atoms, an alkynyl group having up to 8 carbon atoms, an alkoxyl group having up to 8 carbon atoms or a cycloalkyl group having up to 8 carbon atoms, and $R^4$ represents a hydrogen atom, a straight chain or branched alkyl group having up to 8 carbon atoms, a straight chain or branched alkenyl group having up to 8 carbon atoms or an alkynyl group having up to 8 carbon atoms.

13. A herbicidal composition according to claim 8, wherein X represents a fluorine atom, and $R^1$ represents an alkoxyalkyl group having up to 8 carbon atoms.

14. A herbicidal composition according to claim 8, wherein the active ingredient is at least one member selected from the group consisting of:
N-(2,4-dichloro-5-propargyloxyphenyl)teraconimide,
N-(2,4-dichloro-5-allyloxyphenyl)teraconimide,
N-(2,4-dichloro-5-isopropoxyphenyl)teraconimide,
N-(2,4-dichloro-5-methoxyphenyl)teraconimide,
N-[2,4-dichloro-5-(1-methylallyloxy)phenyl]teraconimide,
N-(2-fluoro-4-chloro-5-propargyloxyphenyl)teraconimide,
N-(2-fluoro-4-chloro-5-allyloxyphenyl)teraconimide,
N-(2-fluoro-4-chloro-5-isopropoxyphenyl)teraconimide,
N-(2-fluoro-4-chloro-5-methoxyphenyl)teraconimide,
N-(2-fluoro-4-chloro-5-methoxymethoxyphenyl)teraconimide,
N-[2-fluoro-4-chloro-5-(1-methylallyloxy)phenyl]teraconimide,
N-[5-[1-(N-methoxy-N-methylcarbamoyl)ethylamino]-2-fluoro-4-chlorophenyl]teraconimide,
N-[5-[1-(N,N-diethylcarbamoyl)ethylamino]-2-fluoro-4-chlorophenyl]teraconimide,
N-[5-[1-(N-propoxycarbamoyl)ethylamino]-2-fluoro-4-chlorophenyl]teraconimide, and
N-[5-[1-(N-propargylcarbamoyl)ethylamino]-2-fluoro-4-chlorophenyl]teraconimide.

15. A method for the destruction of undesirable weeds, which comprises applying to said weeds, in an amount of from 0.4 to 100 g/10a in terms of the amount of an active ingredient, a herbicidal composition which comprises as an active ingredient a herbicidally effective amount of an N-substituted phenylteraconimide compound represented by the formula

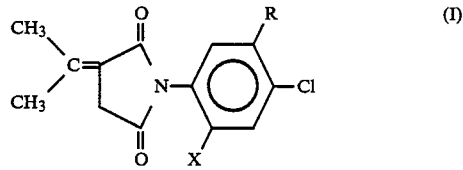

wherein X represents a hydrogen atom, a fluorine atom or a chlorine atom; and

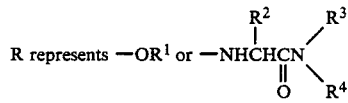

wherein $R^1$ represents a hydrogen atom, a straight chain or branched alkyl group having up to 8 carbon atoms, a straight chain or branched alkenyl group having up to 8 carbon atoms, an alkynyl group having up to 8 carbon atoms, a cycloalkyl group having up to 8 carbon atoms wherein a carbon atom thereof is unsubstituted or substituted with an oxygen atom, a sulfur atom or a carbonyl group, or a straight chain or branched alkyl or alkenyl group having up to 8 carbon atoms and substituted with at least one substituent selected from the group consisting of a halogen atom, a cyano group, a hydroxyl group, an alkoxyl group having up to 8 carbon atoms, an alkylthio group having up to 8 carbon atoms, an epoxy group, a substituted or unsubstituted aromatic hydrocarbon group having up to 8 carbon atoms, an acyl group having up to 8 carbon atoms and an alkoxycarbonyl group having up to 8 carbon atoms, $R^2$ represents a hydrogen atom or a straight chain or branched alkyl group having up to 8 carbon atoms, and $R^3$ and $R^4$ each independently represent a hydrogen atom, a straight chain or branched alkyl group having up to 8 carbon atoms, a straight chain or branched alkenyl group having up to 8 carbon atoms, an alkynyl group having up to 8 carbon atoms, an alkoxyl group having up to 8 carbon atoms, an alkoxyalkyl group having up to 8 carbon atoms, an alkoxycarbonylalkyl group having up to 8 carbon atoms, a cycloalkyl group having up to 8 carbon atoms, a hydroxyalkyl group having up to 8 carbon atoms, a cyanoalkyl group having up to 8 carbon atoms, an aralkyl group having up to 9 carbon atoms or an aryl group having up to 8 carbon atoms, or $R^3$ and $R^4$ are directly bonded with each other, thereby forming with the nitrogen atom bonded therewith a morpholine ring group.

16. A method according to claim 15, wherein X represents a fluorine atom, and $R^1$ represents a straight chain or branched alkyl group having up to 8 carbon atoms, a straight chain or branched alkenyl group having up to 8 carbon atoms or an alkynyl group having up to 8 carbon atoms.

17. A method according to claim 15, wherein X represents a chlorine atom, and $R^1$ represents a straight chain or branched alkyl group having up to 8 carbon atoms, a straight chain or branched alkenyl group having up to 8 carbon atoms or an alkynyl group having up to 8 carbon atoms.

18. A method according to claim 15, wherein x represents a fluorine atom, $R^2$ represents a methyl group, and $R^3$ and $R^4$ are directly bonded with each other, thereby forming with the nitrogen atom bonded therewith a morpholine ring group, or $R^3$ represents a straight chain or branched alkyl group having up to 8 carbon atoms, a straight chain or branched alkenyl group having up to 8 carbon atoms, an alkynyl group having up to 8 carbon atoms, an alkoxyl group having up to 8 carbon atoms or a cycloalkyl group having up to 8 carbon atoms, and $R^4$ represents a hydrogen atom, a straight chain or branched alkyl group having up to 8 carbon atoms, a straight chain or branched alkenyl group having up to 8 carbon atoms or an alkynyl group having up to 8 carbon atoms.

19. A method according to claim 15, wherein x represents a hydrogen atom, $R^2$ represents a methyl group, and $R^3$ and $R^4$ are directly bonded with each other, thereby forming with the nitrogen atom bonded therewith a morpholine ring group or $R^3$ represents a straight chain or branched alkyl group having up to 8 carbon atoms, a straight chain or branched alkenyl group having up to 8 carbon atoms, an alkynyl group having up to 8 carbon atoms, an alkoxyl group having up to 8 carbon atoms or a cycloalkyl group having up to 8 carbon atoms, and $R^4$ represents a hydrogen atom, a straight chain or branched alkyl group having up to 8 carbon atoms, a straight chain or branched alkenyl group having up to 8 carbon atoms or an alkynyl group having up to 8 carbon atoms.

20. A method according to claim 15, wherein X represents a fluorine atom, and $R^1$ represents an alkoxyalkyl group having up to 8 carbon atoms.

21. A method according to claim 15, wherein the compound is at least one member selected from the group consisting of:

N-(2,4-dichloro-5-propargyloxyphenyl)teraconimide,

N-(2,4-dichloro-5-allyloxyphenyl)teraconimide,

N-(2,4-dichloro-5-isopropoxyphenyl)teraconimide,

N-(2,4-dichloro-5-methoxyphenyl)teraconimide,

N-[2,4-dichloro-5-(1-methylallyloxy)phenyl]-teraconimide,

N-(2-fluoro-4-chloro-5-propargyloxyphenyl)-teraconimide,

N-(2-fluoro-4-chloro-5-allyloxyphenyl)teraconimide,

N-(2-fluoro-4-chloro-5-isopropoxyphenyl)teraconimide,

N-(2-fluoro-4-chloro-5-methoxyphenyl)teraconimide,

N-(2-fluoro-4-chloro-5-methoxymethoxyphenyl)-teraconimide,

N-[2-fluoro-4-chloro-5-(1-methylallyloxy)phenyl]-teraconimide,

N-[5-[1-(N-methoxy-N-methylcarbamoyl)ethylamino]-2-fluoro-4-chlorophenyl]teraconimide, N-[5-[1-(N,N-diethylcarbamoyl)ethylamino]-2-fluoro-4-chlorophenyl]teraconimide, N-[5-[1-(N-propoxycarbamoyl)ethylamino]-2-fluoro-4-chlorophenyl]teraconimide, and N-[5-[1-(N-propargylcarbamoyl)ethylamino]-2-fluoro-4-chlorophenyl]teraconimide.

22. A compound according to claim 1, wherein R is $-OR^1$.

23. A herbicidal composition according to claim 8, wherein R is $-OR^1$.

24. A method according to claim 15, wherein R is $-OR^1$.

25. A compound according to claim 1, wherein R is $-O-CH_2-C \equiv CH$ and X is F.

* * * * *